(12) United States Patent
Chudy

(10) Patent No.: US 9,272,796 B1
(45) Date of Patent: Mar. 1, 2016

(54) AUTOMATIC DRUG PACKAGING MACHINE AND PACKAGE-LESS VERIFICATION SYSTEM

(75) Inventor: Duane S. Chudy, Lincolnshire, IL (US)

(73) Assignee: CHUDY GROUP, LLC, Powers Lake, WI (US)

( * ) Notice: Subject to any disclaimer, the term of this patent is extended or adjusted under 35 U.S.C. 154(b) by 415 days.

(21) Appl. No.: 13/004,730

(22) Filed: Jan. 11, 2011

(51) Int. Cl.
*B65B 5/10* (2006.01)
*A61J 7/00* (2006.01)
*G07F 17/00* (2006.01)
*G06F 19/00* (2011.01)

(52) U.S. Cl.
CPC ............ *B65B 5/103* (2013.01); *G07F 17/0092* (2013.01); *G06F 19/3462* (2013.01)

(58) Field of Classification Search
CPC ..... G07F 17/0092; G07F 11/62; G07F 9/026; G06F 19/3462; G06F 19/3456; B65B 5/103; B65B 57/00; G06Q 10/087; G06Q 50/22; A61J 7/0084; A61J 2205/30; A61J 2205/10; G01N 21/9508
USPC ......... 53/53–54, 58, 494–495, 498–501, 507, 53/508; 382/141, 321; 700/244
See application file for complete search history.

(56) References Cited

U.S. PATENT DOCUMENTS

| | | | | |
|---|---|---|---|---|
| 5,502,944 | A | * | 4/1996 | Kraft et al. .......................... 53/55 |
| 5,510,997 | A | * | 4/1996 | Hines et al. .................... 700/224 |
| 5,819,500 | A | * | 10/1998 | Haraguchi et al. .............. 53/154 |
| 5,819,649 | A | | 10/1998 | Townsend et al. |

(Continued)

FOREIGN PATENT DOCUMENTS

| | | |
|---|---|---|
| CA | 2520399 A1 | 7/2004 |
| EP | 1656630 A1 | 5/2006 |

(Continued)

OTHER PUBLICATIONS

Chudy Group, LLC. ATP-71 Automatic Tablet Packager. Brochure. Date: Jun. 2008.

(Continued)

*Primary Examiner* — Andrew M Tecco
(74) *Attorney, Agent, or Firm* — Jansson Munger McKinley & Kirby Ltd.

(57) ABSTRACT

An automatic drug packaging machine and package-less verification system together with methods and apparatus. In embodiments, the system may include an automatic drug packaging machine for packaging one or more drug into ones of separate pouch packages forming a pouch package web. Each pouch package may include information, a machine-readable code, and have a side through which each packaged drug is viewable. An imager adjacent the web is provided to capture an image of each packaged drug within the pouch package. In embodiments, a code reader adjacent the web may read the pouch package machine-readable code. The code reader may be associated with the imager. In an embodiment, the machine-readable code is compared with an expected code for the pouch package and image information of each packaged drug within the pouch package is compared with a reference image corresponding to each packaged drug for a match. In such embodiment, data may be generated for the pouch package responsive to whether the codes match and whether the images match to provide a verification of the pouch package if the comparisons match and, alternatively, a non-verification of the pouch package if at least one of the comparisons do not match.

26 Claims, 27 Drawing Sheets

(56) References Cited

U.S. PATENT DOCUMENTS

| | | | |
|---|---|---|---|
| 5,852,911 | A | 12/1998 | Yuyama et al. |
| 5,875,610 | A | 3/1999 | Yuyama et al. |
| 5,905,652 | A | 5/1999 | Kutsuma |
| 5,964,374 | A | 10/1999 | Yuyama et al. |
| 6,170,230 | B1 | 1/2001 | Chudy et al. |
| 6,324,253 | B1 * | 11/2001 | Yuyama et al. ............. 378/57 |
| 6,330,351 | B1 * | 12/2001 | Yasunaga ................. 382/141 |
| 6,370,841 | B1 | 4/2002 | Chudy et al. |
| 6,373,519 | B1 | 4/2002 | Sybert et al. |
| 6,505,461 | B1 * | 1/2003 | Yasunaga .................. 53/562 |
| 6,535,637 | B1 * | 3/2003 | Wootton et al. ............ 382/190 |
| 6,611,733 | B1 * | 8/2003 | De La Huerga ............ 700/236 |
| 6,625,952 | B1 | 9/2003 | Chudy et al. |
| 6,738,723 | B2 * | 5/2004 | Hamilton .................. 702/128 |
| 7,044,664 | B2 | 5/2006 | Papetti |
| 7,068,301 | B2 | 6/2006 | Thompson |
| 7,102,741 | B2 * | 9/2006 | Ackley et al. ............ 356/237.1 |
| 7,218,395 | B2 | 5/2007 | Kaye et al. |
| 7,430,838 | B2 | 10/2008 | Rice et al. |
| 7,454,880 | B1 * | 11/2008 | Austin et al. .................. 53/411 |
| 7,536,938 | B2 | 5/2009 | Kim |
| 7,540,222 | B2 | 6/2009 | Kim |
| 7,689,465 | B1 | 3/2010 | Shakes et al. |
| 7,743,930 | B2 | 6/2010 | Krohn |
| 7,756,248 | B2 * | 7/2010 | Beckers et al. ............... 378/53 |
| 7,769,221 | B1 | 8/2010 | Shakes et al. |
| 7,792,349 | B2 | 9/2010 | Van Den Brink |
| 7,796,799 | B2 * | 9/2010 | Jorritsma .................. 382/141 |
| 7,805,217 | B2 * | 9/2010 | Chudy et al. ................ 700/237 |
| 7,860,724 | B2 * | 12/2010 | Chudy et al. .................... 705/2 |
| 7,995,831 | B2 * | 8/2011 | Eller et al. .................. 382/142 |
| 8,036,773 | B2 * | 10/2011 | Braun et al. ................ 700/215 |
| RE42,937 | E * | 11/2011 | Lasher et al. ................... 53/55 |
| 8,146,747 | B2 * | 4/2012 | Luciano et al. .............. 206/534 |
| 8,271,128 | B1 | 9/2012 | Schultz |
| 8,302,370 | B1 | 11/2012 | Decker et al. |
| 8,380,346 | B2 * | 2/2013 | Chudy et al. ................ 700/242 |
| 2004/0088187 | A1 * | 5/2004 | Chudy et al. .................... 705/2 |
| 2005/0125097 | A1 * | 6/2005 | Chudy et al. ................ 700/236 |
| 2006/0213816 | A1 * | 9/2006 | Jorritsma ................... 209/576 |
| 2006/0277269 | A1 * | 12/2006 | Dent et al. .................. 709/217 |
| 2008/0312957 | A1 * | 12/2008 | Luciano et al. .................. 705/2 |
| 2009/0210247 | A1 * | 8/2009 | Chudy et al. .................... 705/2 |
| 2009/0321296 | A1 * | 12/2009 | Luciano et al. .............. 206/534 |
| 2010/0030371 | A1 | 2/2010 | Chudy et al. |
| 2010/0030667 | A1 | 2/2010 | Chudy et al. |

FOREIGN PATENT DOCUMENTS

| | | |
|---|---|---|
| JP | 60033036 A | 2/1985 |
| JP | 63294307 A | 12/1988 |
| JP | 4025748 A | 1/1992 |
| JP | 5337168 A | 12/1993 |
| JP | 7200770 A | 8/1995 |
| JP | 7209196 A | 8/1995 |
| JP | 7262379 A | 10/1995 |
| JP | 7282219 A | 10/1995 |
| JP | 8168727 A | 7/1996 |
| JP | 2000186915 A | 7/2000 |
| JP | 2005227302 A | 8/2005 |
| JP | 2006189354 A | 7/2006 |
| JP | 2006292419 A | 10/2006 |
| WO | WO0225568 A2 | 3/2002 |
| WO | WO2005017814 A1 | 2/2005 |

OTHER PUBLICATIONS

Chudy Group, LLC. The ATP-Series Automated Tablet Packaging Solutions. Brochure. Undated.
Knapp UK LTD. Error-Free Handling: Logistics' Holy Grail. <<www.knapp.com>> Date: Copyright 2010.
YouTube Video titled "ZiuZ Foresee Inspector (www.ziuzmedical.com)" upload by Jelle Waringa on Jan. 15, 2010; retrieved from the Internet on Jun. 25, 2014; URL: http://www.youtube.com/watch?v=28s97N4Pzz0.
YouTube Video titled "ZiuZ Inspector" upload by Jelle Waringa on May 17, 2011; retrieved from the Internet on Jun. 25, 2014; URL: http://www.youtube.com/watch?v=OpENWpp_gA8.
Vimeo Video titled "ZiuZ Inspector" upload by ZiuZ on Jun. 15, 2011; retrieved from the Internet on Jun. 23, 2014; URL: http://vimeo.com/25125298.
Ziuz Medical B.V., "ZiuZ Medical Systems," retrieved from the internet Feb. 28, 2014; URL: http://medical.ziuz.com/en.
EPLAW Patent Blog, "NL—Global Factories v. Ziuz." URL: http://www.eplawpatentblog.com/eplaw/2010/12/nl-global-factories-v-ziuz; dated Sep. 12, 2010.

* cited by examiner

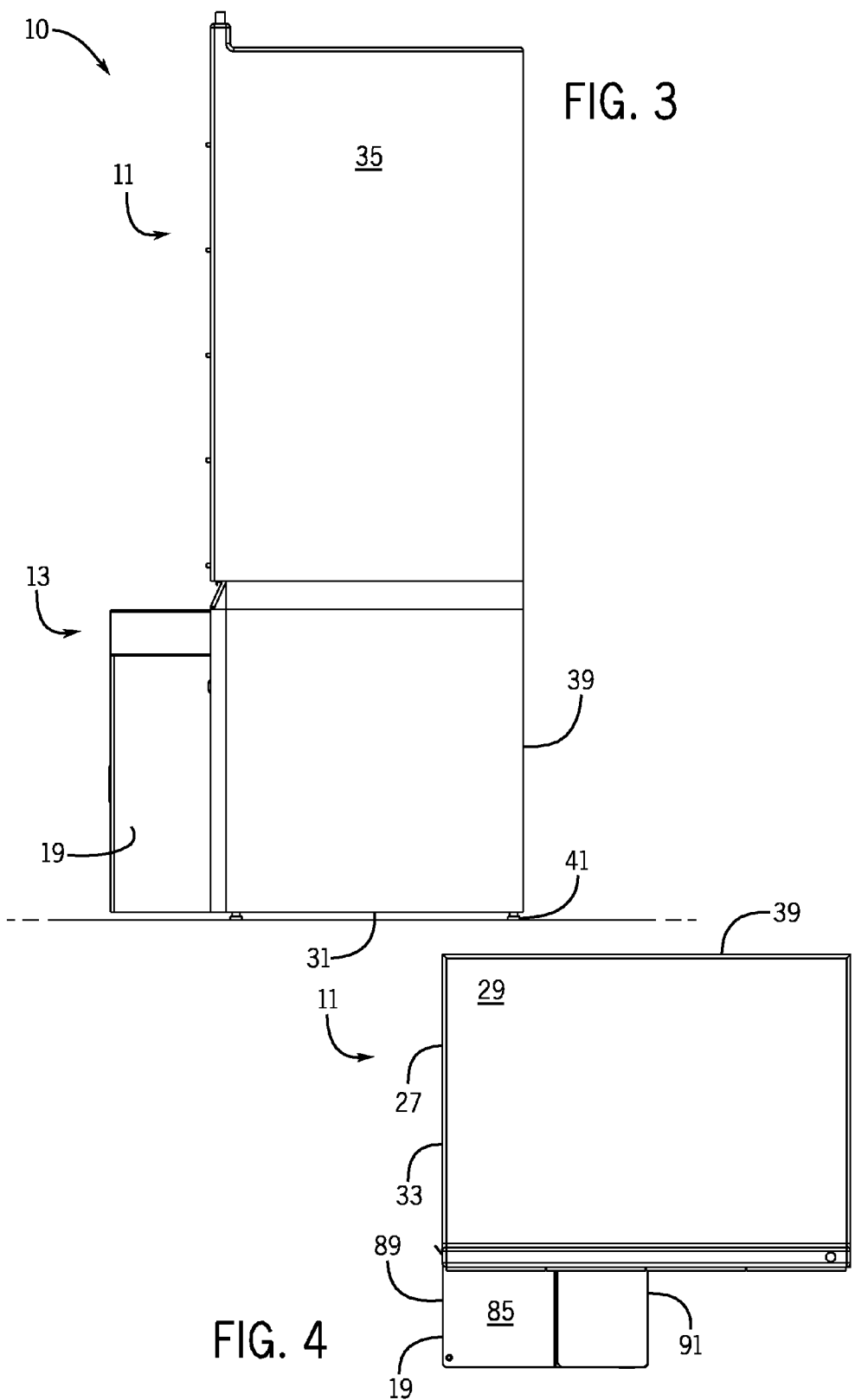

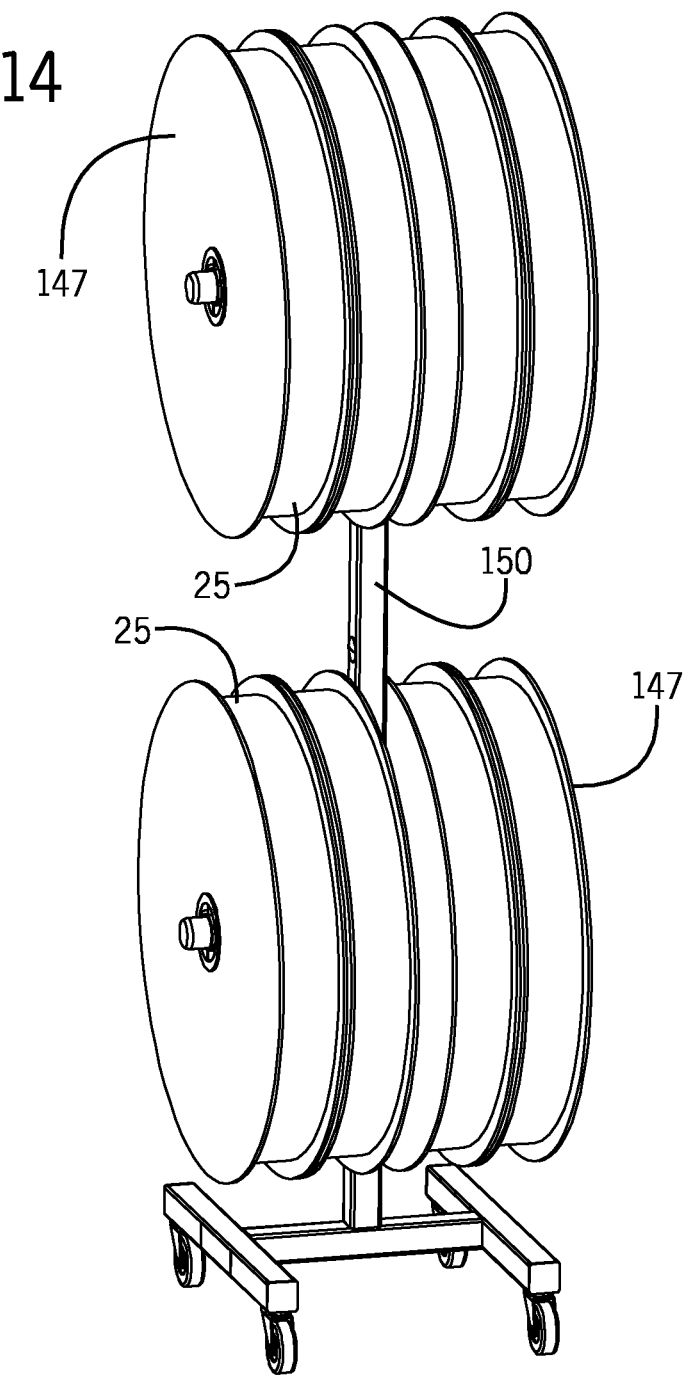

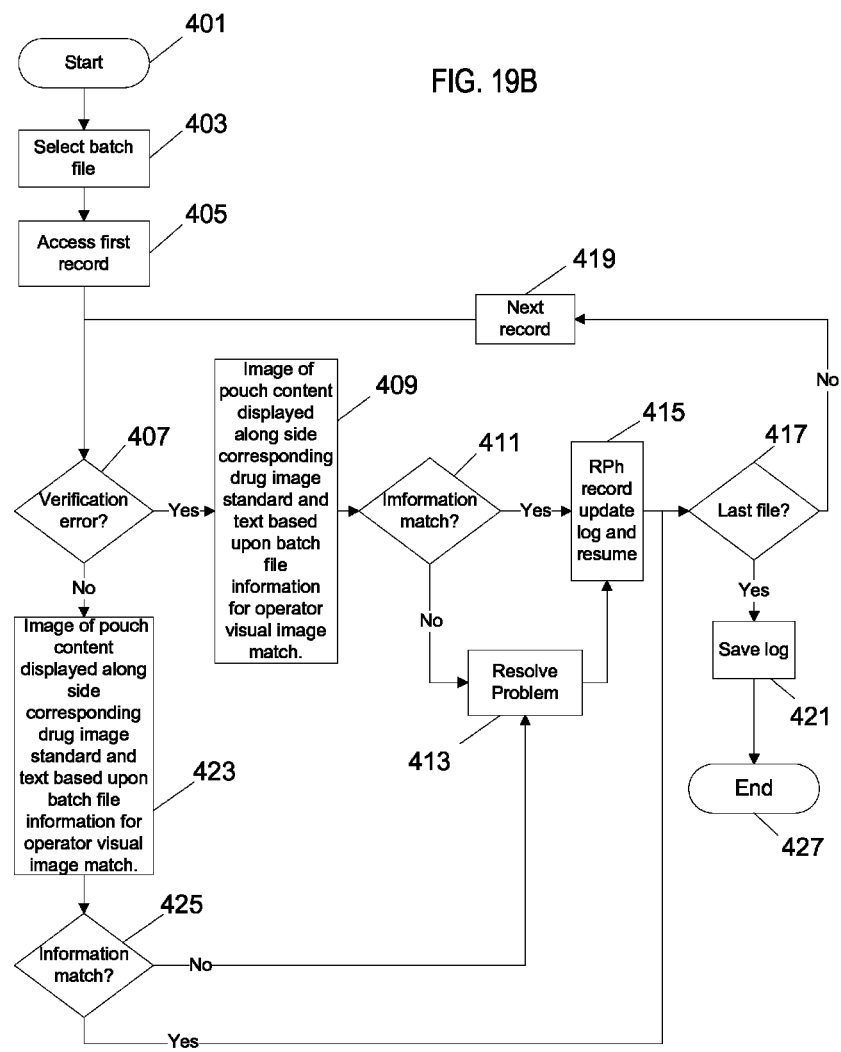

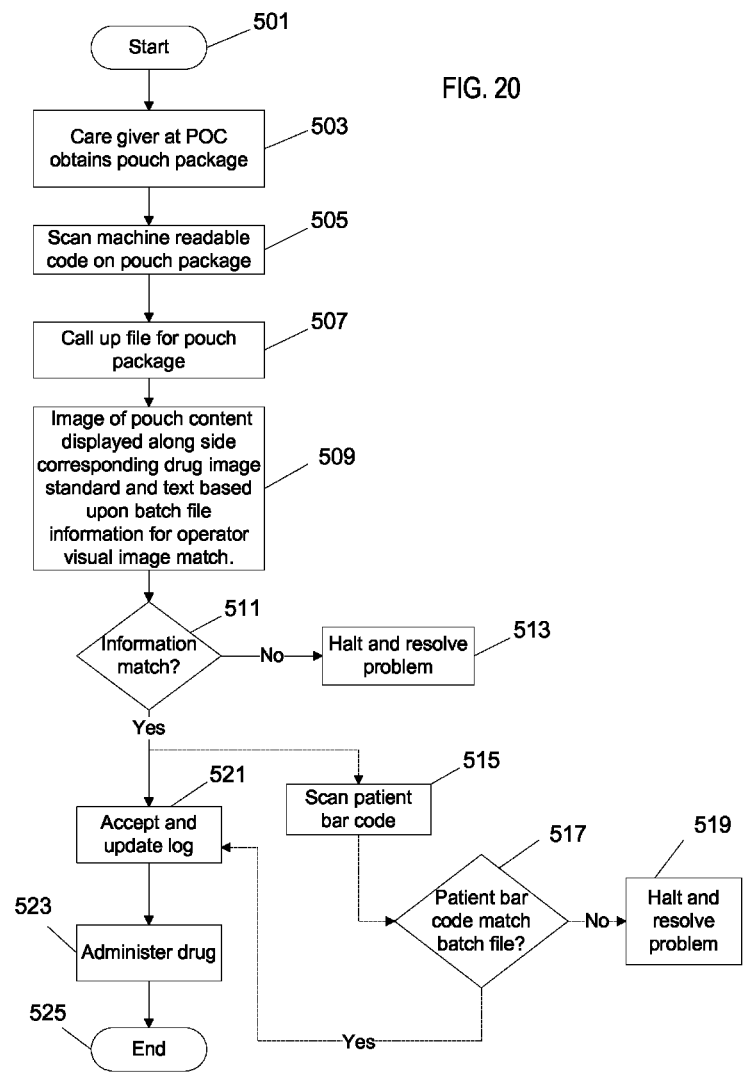

AUTOMATIC DRUG PACKAGING MACHINE AND PACKAGE-LESS VERIFICATION SYSTEM

FIELD

The field relates generally to automatic drug packaging and, more particularly, to systems for verification that the drugs are packaged correctly.

BACKGROUND

Prescription order fulfillment and administration of drugs to patients are important tasks which require the exercise of considerable care to ensure that the patient receives the correct drug in accordance with the physician's instructions. Because of the importance that prescription orders be fulfilled correctly, a registered pharmacist is required to review each prescription order and to verify that the prescription order has been fulfilled correctly. This prescription order review and verification process is performed before the prescription order is provided to the patient and before any drugs are administered to the patient to ensure that the patient receives the appropriate medical treatment.

Registered pharmacist prescription order review and verification is a time-consuming and relatively costly process. The registered pharmacist review and verification process can increase the cost of delivering high-quality patient care. The healthcare industry is under constant pressure to control these costs. Moreover, registered pharmacists are highly-skilled professionals whose time is valuable and can be spent, for example, performing other important tasks such as counseling patients.

Pharmacies are increasingly reliant on automation in order to improve the quality of patient care and to control healthcare costs. One highly-effective application of pharmacy automation is the use of automatic drug dispensing and packaging machines, referred to herein simply as automatic drug packaging machines. The automatic drug packaging machines may package the drugs in what are known as "compliance packages." Compliance packages organize the drugs in some useful manner to facilitate compliance with the physician's instructions.

One type of compliance package output by an automatic drug packaging machine is referred to in industry as a "pouch package." Pouch packages are formed serially in a web of pouch packaging material with each pouch package containing a drug "dose" consisting of one or more drugs. The drugs may be in tablet form or in other forms, such as granular or powdered form. The web of pouch packages output from the automatic drug packaging machine is sometimes referred to as a "vine." Each pouch package is a separate, sealed drug-containing package formed in the pouch package web, or vine. The pouch package web can be as long as required by the pharmacy or other automatic drug packaging machine operator. To facilitate compliance, the automatic drug packaging machine prints useful information on each pouch package, such as the patient name, drug information, and instructions for administration of the drug. The automatic drug packaging machine is computer controlled and may be programmed to output any number and sequence of pouch packages. An automatic drug packaging machine can operate for many hours, for example overnight, without human intervention.

Pouch packages are a useful type of compliance package because the packages may be output from the automatic drug packaging machine ordered in any suitable manner, such as by the particular time of day at which the drug in each pouch is to be taken, (e.g., breakfast, lunch, and dinner). The pouch package web may be cut into smaller portions corresponding to each patient's prescription order and then may be provided to the patient. The patient then takes each drug one-after-the-other in the sequence in which the pouch packages are provided.

Pouch-package-type compliance packages are highly effective for drug administration at in-patient facilities, such as hospitals and long-term care facilities (e.g., nursing homes). This is because the pouch packages can be generated for many patients and can be grouped and organized in order of administration, thereby facilitating implementation of the physician's instructions and improving the quality of patient care.

While automatic drug packaging machines are excellent for their intended purpose, any automatic process carries with it the possibility of incorrect operation. For example, there may be a rare circumstance in which the wrong drug is packaged in the pouch package. There may be a rare circumstance in which a mismatch exists between a given pouch and the drug expected to be loaded in that pouch, potentially causing a series of drug and pouch package mismatches. There is also a limited possibility of printer error or malfunction so that the information printed on each package is not legible, or is unusable.

In these rare circumstances, pharmacy personnel must take corrective steps because the drugs cannot be administered unless the pharmacy is confident that the prescription order is correct and that any important printed information is usable. The corrective steps could involve discarding the pouch packages or expending valuable human time to manually remove the drugs from the pouch packages and to restock the drugs.

As valuable as automatic drug packaging machines are, the foregoing infrequent issues illustrate the importance of registered pharmacist prescription order review and verification before the pouch packages comprising a patient prescription order are administered to a patient. This review and verification is routinely performed by manually handling and checking each pouch package against printed or displayed information corresponding to the patient prescription order.

As can be appreciated, manual handling and review and verification of pouch packages is a slow and tedious process. Each pouch package web, or vine, may include many hundreds of look-alike pouch packages. The manual review and verification process is potentially subject to error because of the repetitive nature of the process and the look-alike appearance of the pouch packages. Therefore, while automatic drug packaging machines provide improvements in dispensing and packaging of the drugs, the prescription order fulfillment process is not optimally efficient because of the limitations imposed by the manual review and verification process of the pouch packages output from the automatic drug packaging machine.

Various inspection devices have been proposed to facilitate pouch package inspection. For example, U.S. Pat. No. 6,330,351 describes a pouch package drug inspection device in which a camera-generated image of the actual pouch package content is compared with a reference image of the content. However, the drug inspection device is disadvantageous at least because it is incapable of detecting pouch package loading errors in real time as the pouch packages are output from the automatic tablet packaging machine.

A further pouch package inspection device is described in U.S. Pat. No. 7,540,222. This patent describes a manual inspection system in which a user manually examines an enlarged camera-generated image of each pouch package for printing errors or for broken tablets. The inspection device is disadvantageous, however, at least because it is limited to manual detection of printing and tablet-damage errors and is not a prescription order verification system.

There is a need for an automatic drug packaging machine and package-less verification system which would address some or all of the foregoing needs, including needs of in-patient facility pharmacies and pharmacies generally, which would facilitate reliable and accurate prescription order review and verification, which would reduce the cost of prescription order review and verification, which would provide automatic "real time" detection of packaging errors thus avoiding creation of incorrectly-packaged pouch package webs, which would permit rapid and accurate verification of each pouch package without the need to physically handle any pouch package, and which would generally improve the quality of patient care.

SUMMARY

Exemplary systems, methods, and apparatus for an automated drug packaging machine and package-less verification system are described herein. In an embodiment, there is provided an automatic drug packaging machine and package-less verification system. In a preferred embodiment, an automatic drug packaging machine preferably includes a support structure and a packaging apparatus. In such embodiment, the packaging apparatus is provided to package one or more drug into ones of separate pouch packages. The pouch packages preferably form a pouch package web. In such preferred embodiment, each pouch package has associated information, a machine-readable code, and a side through which each packaged drug is viewable.

The preferred embodiment preferably includes an imager secured with respect to the support structure adjacent the web. The imager preferably captures an image of each packaged drug within the pouch package. The embodiment preferably further includes a code reader secured with respect to the support structure adjacent the web to read the pouch package machine-readable code. The preferred embodiment also preferably includes a computer programmed with instructions for performing a method of package-less verification of the pouch package.

In such preferred embodiment, the method implemented by the instructions comprises capturing an image of the pouch package side and each packaged drug viewable through the side, associating the image of the pouch package side and each packaged drug viewable through the side with a file for the pouch package, the file preferably including a code corresponding to the machine-readable code, reading the pouch package machine-readable code with the code reader, and comparing the codes for a match. The method may further include comparing the image of the pouch package side and each packaged drug viewable through the side with a reference image corresponding to each packaged drug for a match. The method may further include generating data for the pouch package responsive to whether the codes match and whether the images match, the data including at least a verification of the pouch package if the comparisons match and, alternatively, a non-verification of the pouch package if at least one of the comparisons do not match.

Preferably, the generating of data for the pouch package responsive to whether the codes match occurs automatically after reading the pouch package machine-readable code, thereby providing the pharmacy or operator with an opportunity to immediately detect a pouch package error before a long, incorrect pouch package web is generated.

In embodiments, the automatic drug packaging machine further comprises a module. In an embodiment, the module preferably includes the support structure, and the imager and code reader are preferably secured to the support structure within the module. In embodiments, the module is capable of being secured to an automatic drug packaging machine housing. In embodiments, the module may be a component separate from the automatic drug packaging machine. Preferably, the determination of whether the codes match implemented by the instructions occurs before the pouch package exits the module. Preferably, a record is created of the pouch package verification or non-verification. The record may be created in the file for the pouch package.

Various actions may be taken if the codes do not match. For example, an alarm may be generated or the process may be stopped if the codes do not match. By way of further example, a modification of the pouch package may be provided if the codes do not match to facilitate identification of the pouch package. In an embodiment, the modification may include an identification mark made on the pouch package.

In yet another embodiment, a classification code may be provided on the pouch package. For example, the pouch package could be color coded to indicate the time of day that the drug is to be administered.

In another embodiment, a message package may be provided in the pouch package web proximate the pouch package. An exemplary message package may include information relating to the pouch package.

In other aspects, a pouch package may be provided in which the information associated with the pouch package is on the side through which each packaged drug is viewable and the information and each packaged drug are viewable simultaneously. In this embodiment, information and the appearance of the packaged drug could appear in a single captured image.

It is preferred that the machine-readable information of the pouch package is a barcode. The code reader may be a barcode reader. In an embodiment, the imager may be the code reader. For example the imaging device may include the code reader as a component or capability.

In other aspects, the package-less verification system further comprises a display. The display may be utilized, for example, to compare: the image of the pouch package side, each packaged drug viewable through the side, and a reference image corresponding to each packaged drug for a match. The display may be at a workstation.

In embodiments, the automatic drug packaging machine is at a first location and the display is at a second location spaced from the first location. This capability permits the package-less verification to be performed by a pharmacist in, for example, a city or state far from the automatic drug packaging machine without the necessity to have the pouch package physically present for verification.

In yet another embodiment, the imager may be configured to capture an image of information on a first side of the pouch package and to capture an image of each drug visible through the pouch package second side. In such an embodiment, the imager may comprise a first imaging device and a second imaging device. The first imaging device is preferably secured with respect to the support structure adjacent the web to capture an image of the information on the pouch package first side. The second imaging device is preferably secured with respect to the support structure adjacent the web to capture the image of the pouch package second side and each packaged drug viewable through the second side. Images of the first and second sides may be captured and the images of the pouch package first side and the pouch package second side may be compared with a reference image during the verification process. The comparing may occur on a display.

In other embodiments, an image of the pouch package first side and an image of the pouch package second side may be associated with the file for the pouch package. It is further preferred that a record is created in the file that the pouch package has been verified as correct by a user, thereby creating an archive that the pouch package has been verified.

It is preferred that the system further comprises a printer and the computer programmed with instructions for performing a method further includes printing the information on a side of the pouch package. The printing may be on the side through which the drugs are visible, or an opposite side.

In yet another aspect, the printed information may include a registration mark detectable by the imager. Detection of the registration mark may be used to trigger capture of an image of a pouch package and reading of the pouch package machine-readable code. The information on the pouch package including the registration mark may be positioned on the pouch package based on a selected pouch package size so that the information is in an appropriate position for imaging by the imager.

Further exemplary systems, methods, and apparatus for an automated drug packaging machine and package-less verification system may be implemented in accordance with the principals described herein.

BRIEF DESCRIPTION OF THE DRAWINGS

Exemplary systems, methods, and apparatus for an automated drug packaging machine and package-less verification system may be understood by reference to the following description taken in conjunction with the accompanying drawings, in which like reference numerals identify like elements throughout the different views. The drawings are not necessarily to scale, emphasis instead being placed upon illustrating the principles of the invention. The drawings depict only embodiments of the invention and are not therefore to be considered to be limiting of the scope of the invention. In the accompanying drawings:

FIG. 3 is a side elevation view of the exemplary automatic drug packaging machine and package-less verification system of FIG. 1;

FIG. 4 is a top plan view of the exemplary automatic drug packaging machine and package-less verification system of FIG. 1;

FIG. 6A is a schematic illustration of exemplary cassette, motor base, hopper, and optional drug counter apparatus of the automatic drug packaging machine of FIGS. 1-5;

FIG. 14 is a perspective view of an exemplary storage and moving rack, shown loaded with plural spools containing packaged pouch package web;

FIG. 19B is a flow diagram showing exemplary methods of delayed time package-less verification; and FIG. 20 is a flow diagram showing an exemplary method of point of care verification.

DETAILED DESCRIPTION

Figure 1:
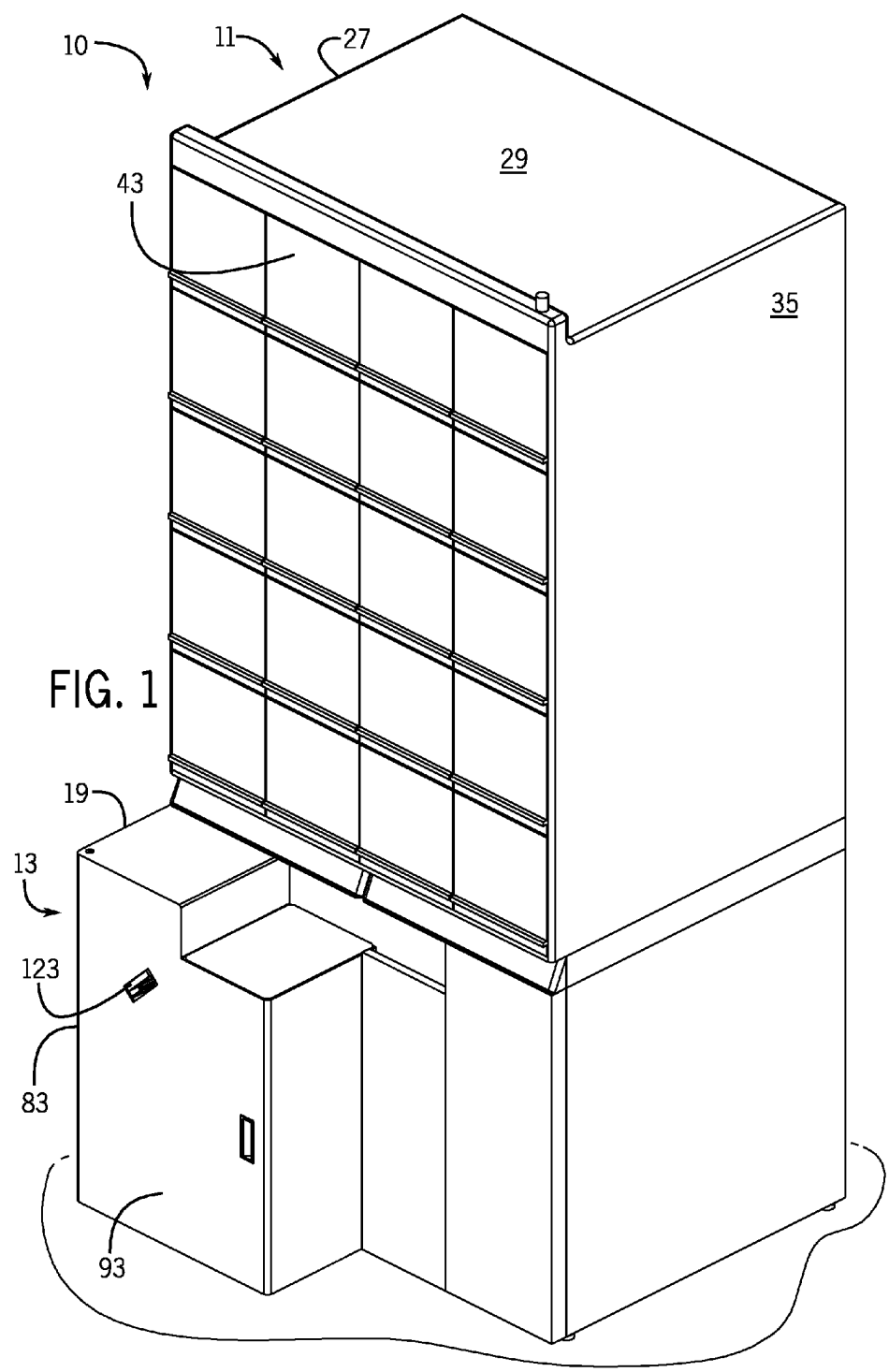
FIG. 1 is a perspective view of an exemplary automatic drug packaging machine and package-less verification system.

An exemplary automatic drug packaging machine and package-less verification system 10 will first be described with respect to FIGS. 1-13A. As used herein, "package-less" means or refers to having the capability to verify that the patient prescription order is correct without the necessity to physically handle or touch the drug or drug container during the verification process. The exemplary automatic drug packaging machine and package-less verification system 10 provides for improved error detection during the prescription order fulfillment process, both in terms of providing improved confidence that the prescription order is correct and in decreasing the time required to verify that the prescription order is correct. As a result, demands on the registered pharmacist and pharmacy personnel generally are decreased, health care costs are controlled, and the quality of patient care is improved.

It should be understood that several preferred embodiments of the present invention are described herein and they are thus representative of the subject matter which is broadly contemplated by the present invention. The scope of the present invention fully encompasses other embodiments and equivalents. Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention. Features and advantages of the present invention will become more fully apparent from the following description and appended claims.

Automatic Drug Packaging Machine and Package-Less Verification System

Referring then to FIGS. 1-13A, the exemplary automatic drug packaging machine and package-less verification system 10 comprises an automatic drug packaging machine 11 and a package-less verification system 13. Exemplary system 10 further comprises a computer 15 with a central processing unit ("CPU") and associated non-volatile memory 17. Computer 15 is programmed with a set of instructions, which may be in non-volatile memory 17, for execution by system 10. Computer 15 may, for example, consist of a main frame, a server, an off-the-shelf personal computer ("PC"), or plural operably-connected servers or PCs. One of ordinary skill in the art will appreciate that computer 15 can be dedicated to system 10 or can be a computer which is shared by multiple modules, including a pharmacy information system which controls the overall operation of a pharmacy operating the system.

In an embodiment, verification system 13 may be integrated with the automatic drug packaging machine 11. In a further embodiment, such as the example of FIGS. 1-13, the verification system 13 may be provided in the form of a modular component 19 added to the automatic drug packaging machine 11. It is expressly contemplated that such a modular component 19, including some or all portions of the package-less verification system 13, may be provided as a component separate and apart from the automatic drug packaging machine 11. This latter arrangement permits an automatic drug packaging machine 11 to be retrofit and upgraded with a package-less verification system 13. Moreover, module 19 is exemplary only. It is further expressly contemplated that the package-less verification system 13 may be provided in a form other than module 19.

In the example and as illustrated in FIGS. 2, 6, 12-14, and 15A-16F, the automatic drug packaging machine 11 dispenses and packages one or more drug 21 in individual ones of separate pouch packages 23. In other words, one or more drug 21 is contained in each pouch package 23. As used herein, "drug" includes any medicament and chemical substance used in the treatment, cure, prevention, or diagnosis of disease or used to otherwise enhance physical or mental well-being, and can include nutriceuticals such as vitamins and supplements. Each pouch package 23 is formed serially in a pouch package web 25, also referred to herein as a web or a vine.

The pouch packages 23 may be provided as compliance packages to facilitate patient compliance with the physician's instructions as set forth in a prescription. To this end, a vine may be organized and arranged so that each pouch package 23 and drug 21 in each pouch package 23 are in the order in which each drug 21 is to be taken. Each pouch package 23 may be organized in any other manner desired by the pharmacy or other operator. For example, all pouch packages 23 for patients in a hospital ward or long-term care facility ward could be organized by room number in the order in which the drugs 21 are to be administered to the patient in each room.

As an alternative, the pouch packages 23 can be loaded with drugs 21 not associated with any prescription order. For example, the pouch packages 23 may be loaded serially with identical drugs 21 such as a commonly-provided pain medication.

Referring again to FIGS. 1-13, exemplary automatic drug packaging machine 11 includes a housing 27 with top and bottom walls 29, 31, left and right sidewalls 33, 35, and front and rear walls 37, 39. Automatic drug packaging machine 11 may be supported on a floor by legs 41. A touch-screen video display (not shown) may be mounted to housing 27 and may include controls permitting a technician or pharmacist to control operation of the automatic drug packaging machine 11 and to receive information about the status of the drug fulfillment process.

Exemplary automatic drug packaging machine 11 includes twenty pull-out drawers. For convenience and brevity, reference number 43 is used for each drawer. In the example, the drawers 43 are organized into five rows of four drawers. As illustrated schematically in FIG. 6A, each drawer 43 supports a plurality of cassettes which may be removable from the respective drawer 43. The cassettes 45 are also referred to in industry as "canisters."

Each cassette 45 stores a quantity of loose, flowable drugs 21. The drugs 21 are typically in a form referred to as a "tablet." The tablet-form drugs 21 may be in any shape including capsules, spheres, ovals, disks, multi-angles, squares, triangles, ellipses, and the like. The tablet-form drugs 21 could be provided as single-dose tablets or as partial dose tablets. For example, tablets could be cut in half to provide a half-strength dose of the drug 21. While not illustrated, an automatic drug packaging machine 11 embodiment could also be configured to dispense drugs in forms other than tablets, such as granular or powdered form. The cassettes 45 can be replenished as drugs 21 stored therein are depleted.

As illustrated schematically in FIG. 6A, each cassette 45 may be associated with a motorized base 47. Each base 47 may be supported on one of the pull-out drawers 43. This arrangement permits a technician to easily pull out a drawer 43 to service any base 47 and to remove any cassette 45 for drug 21 replenishment.

Each motor base 47 may be activated to dispense the needed drug quantity for each pouch package 23. The motor base 47 may include a rotatable platen (not shown) or rotatable comb (not shown) which meters (i.e., singulates) drugs 21 from a cassette 45 one-after-the-other. The motor base 47 includes a counter 49, which may be an infra-red emitter and detector pair, which registers a count each time a drug 21 passes the counter 49. The count is used to control operation of the motor base 47 (i.e., turn the motor base 47 "off") so that the correct quantity of drugs 21 is dispensed from cassette 45 for each pouch package 23.

Automatic drug packaging machine 11 may include apparatus other than plural cassettes 45 for storing and dispensing drugs 21. For example the automatic drug packaging machine 11 could store and dispense drugs 21 from an exception storage apparatus (not shown), also referred to as a universal tray. An exception storage apparatus may be a pull-out device with drugs 21 stored in separate apparatus compartments. The exception storage apparatus dispenses the stored drugs 21 one-after-the-other under control of the automatic drug packaging machine 11. The exception storage apparatus may be particularly effective in dispensing partial dose tablets, such as the previously-described tablets which have been cut in half to provide a half-strength dose of the drug 21.

Figure 6:
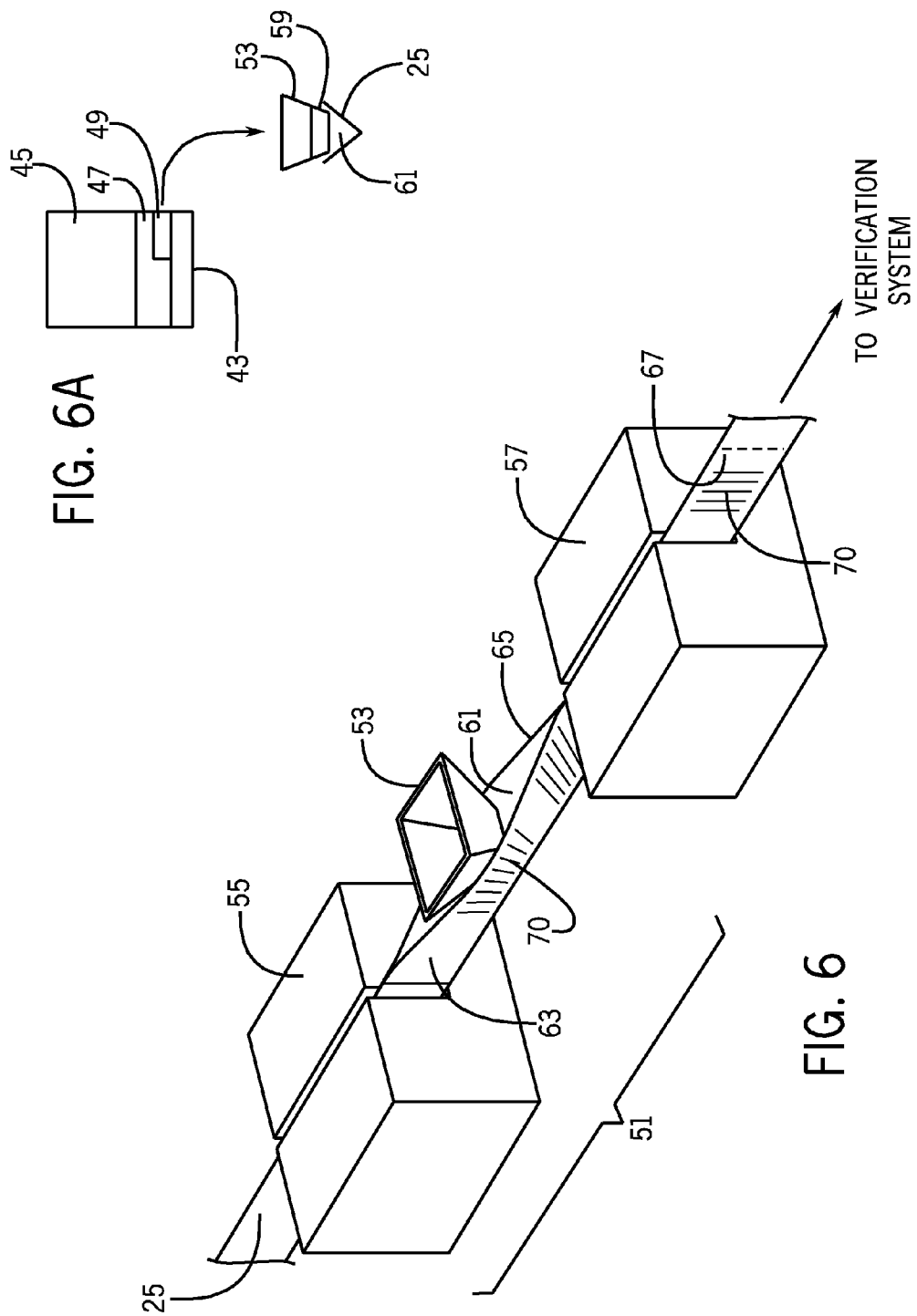
FIG. 6 is a schematic illustration of an exemplary packaging apparatus of the exemplary automatic drug packaging machine and package-less verification system of FIGS. 1-5.
Figure 7:
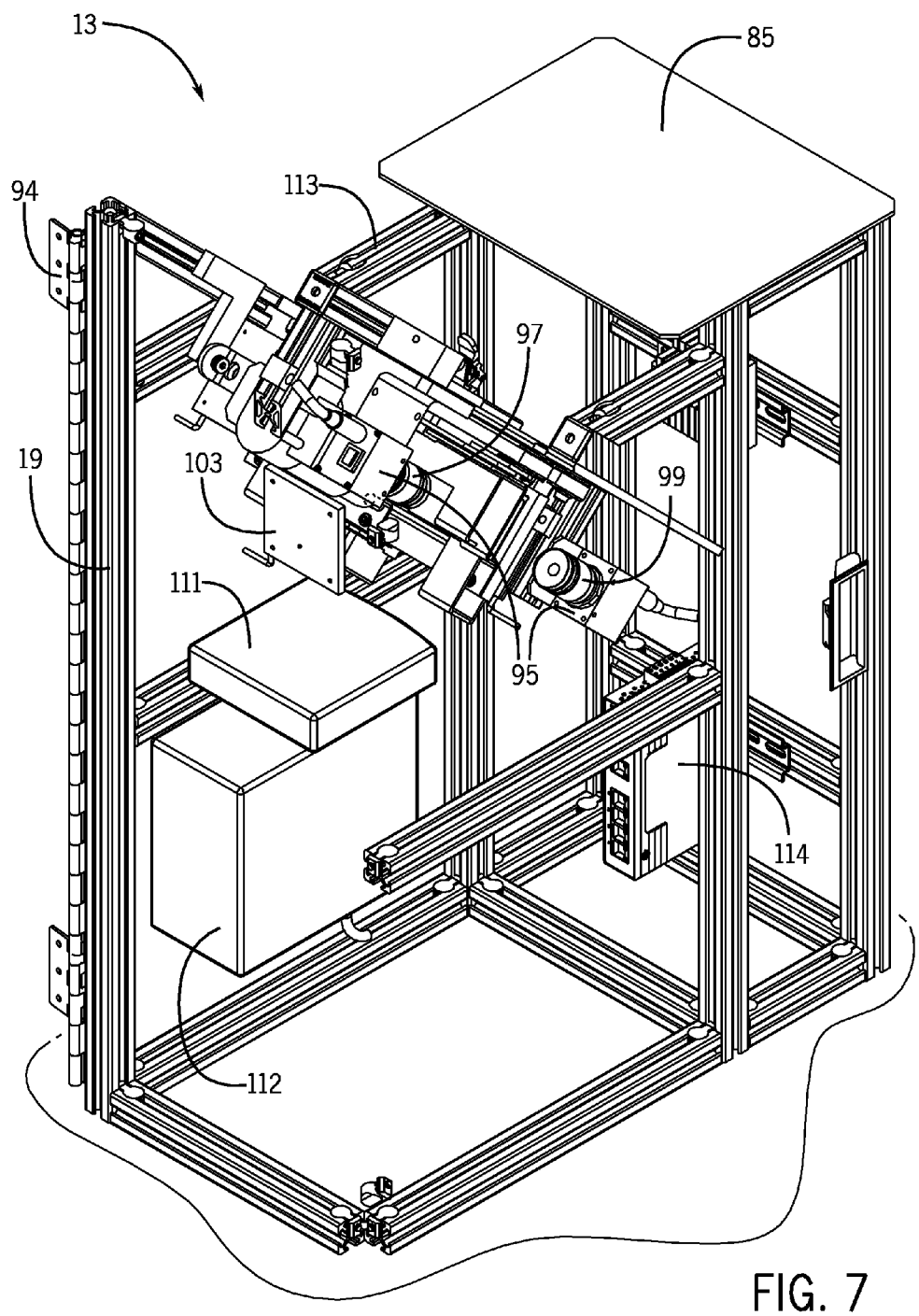
FIG. 7 is a fragmentary left side perspective view of the exemplary pouch package verification system module of FIGS. 1-5.
Figure 8:
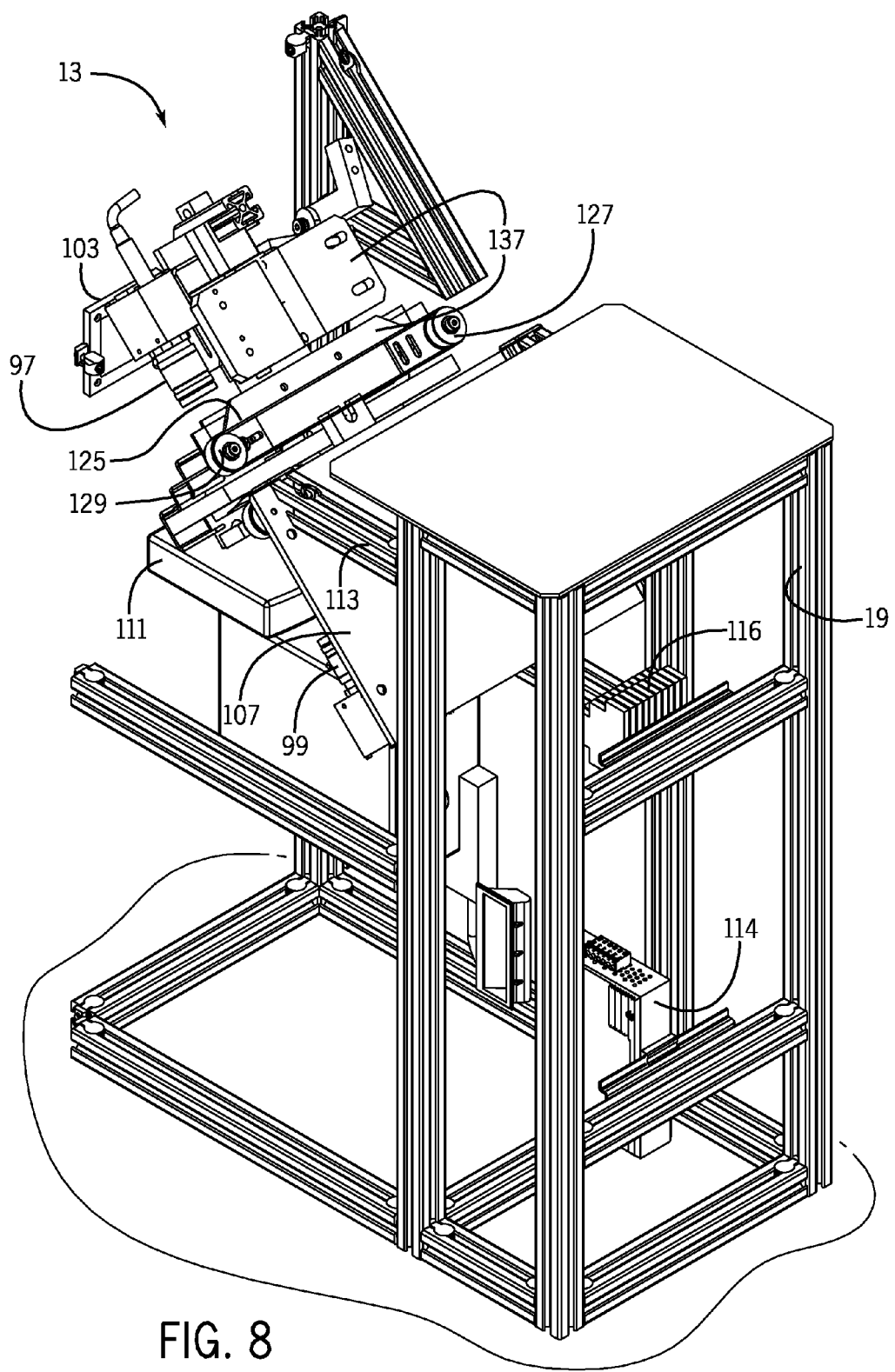
FIG. 8 is a fragmentary right side perspective view of the exemplary pouch package verification system module of FIGS. 1-5.
Figure 9:
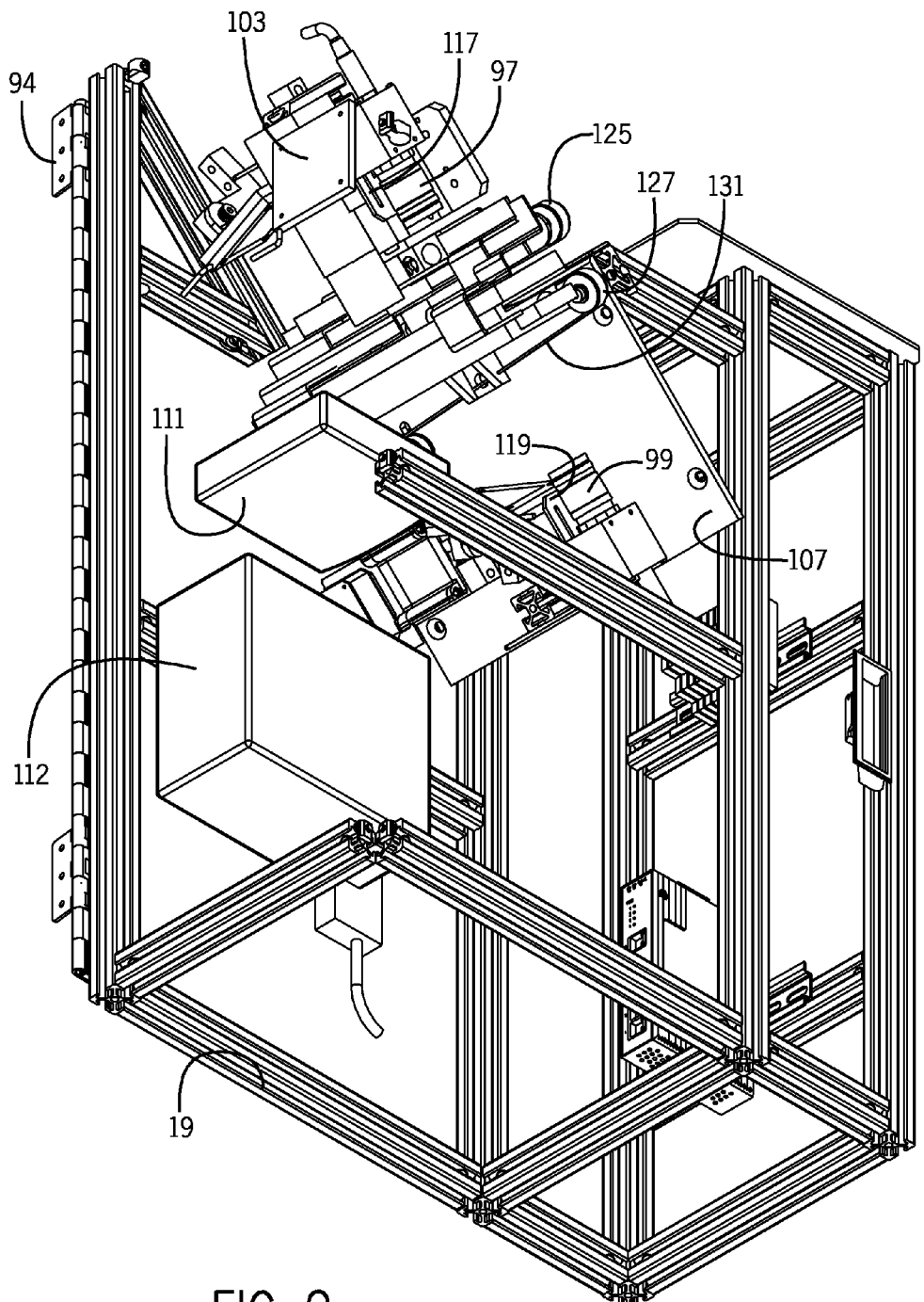
FIG. 9 is a fragmentary bottom side perspective view of the exemplary pouch package verification system module of FIGS. 1-5.
Figure 10:
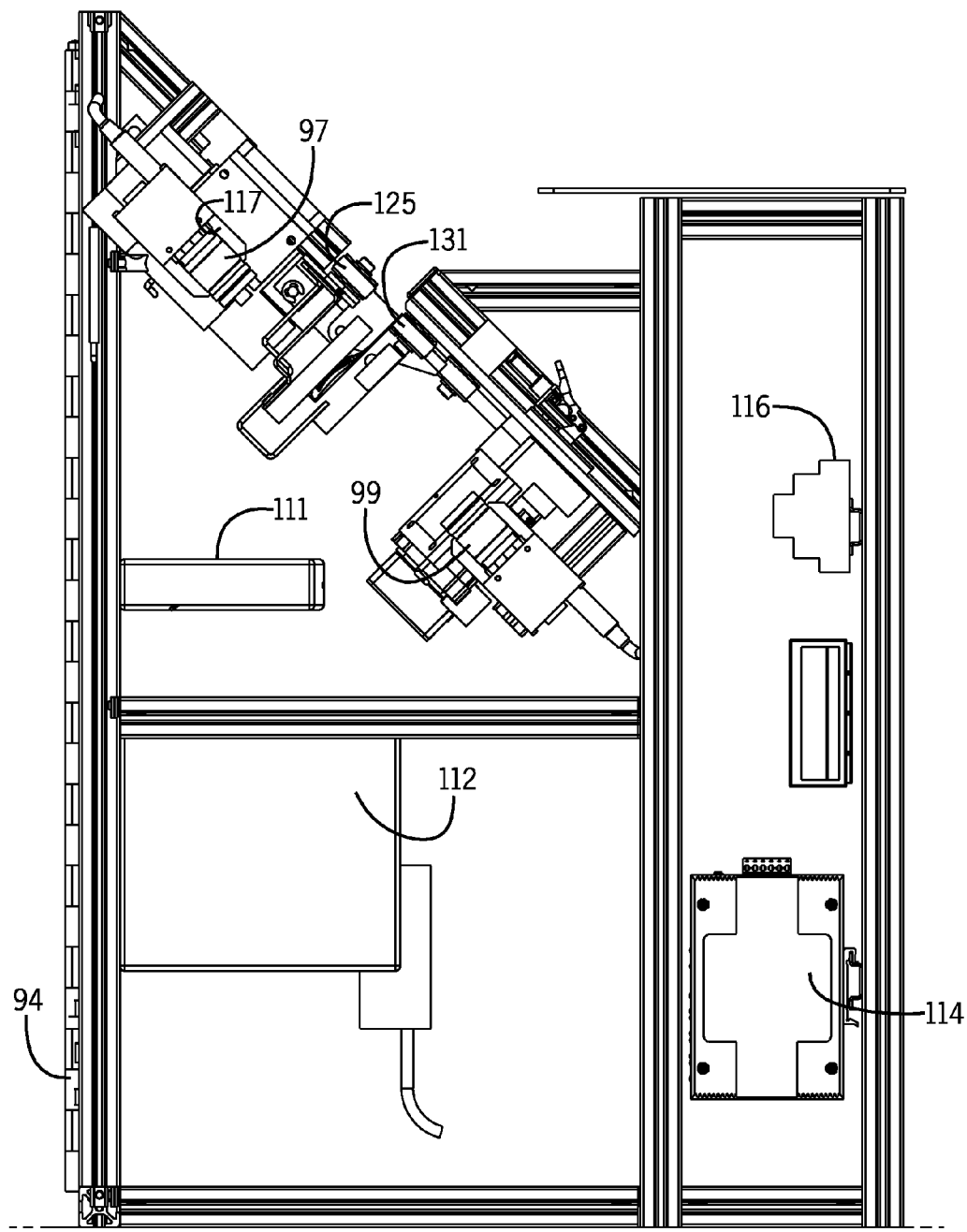
FIG. 10 is a fragmentary front elevation view of the exemplary pouch package verification system module of FIGS. 1-5.
Figure 11:
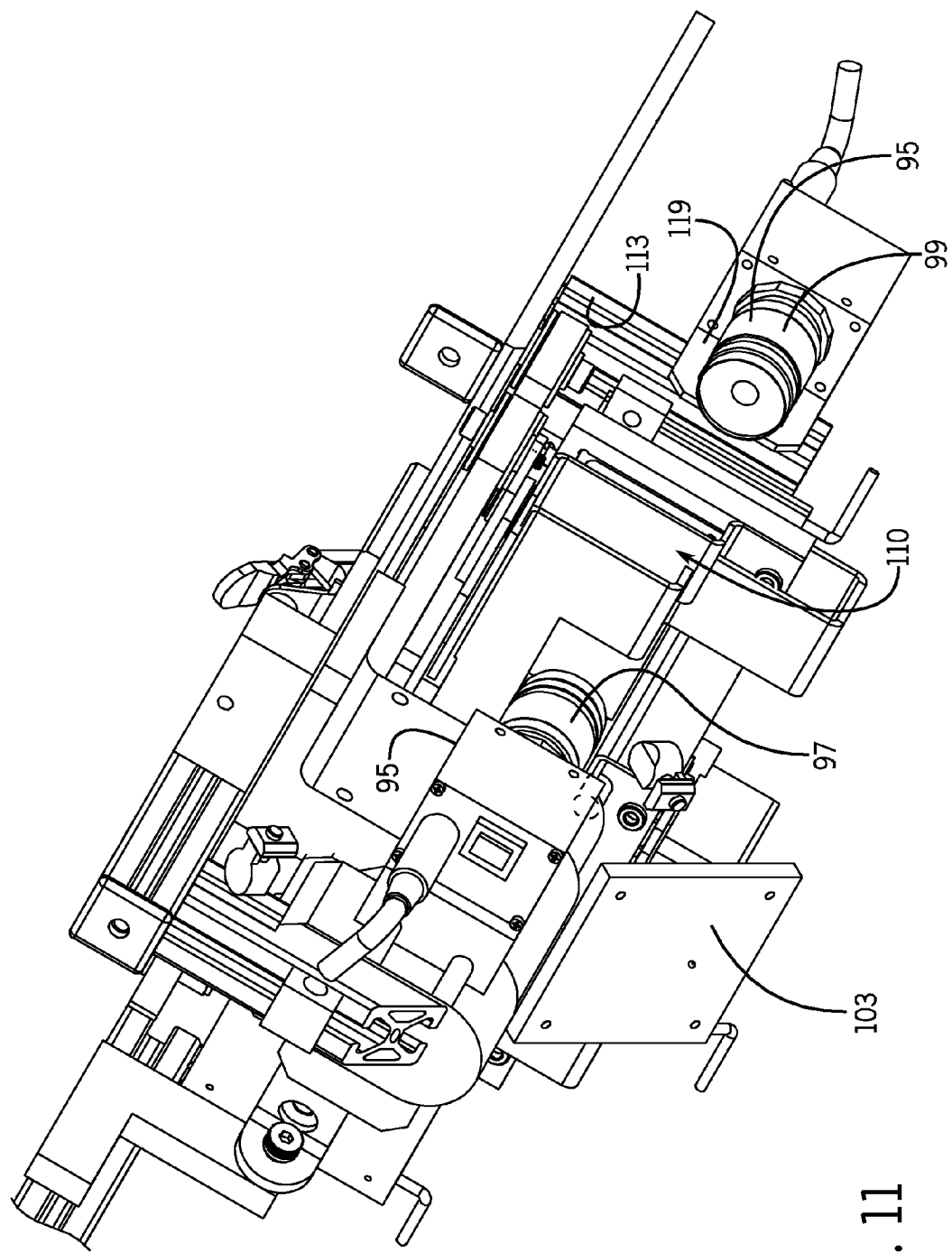
FIG. 11 is an enlarged fragmentary view of imaging devices, a web guide and other components of the exemplary pouch package verification system module of FIGS. 1-5.

FIG. 6 schematically illustrates a packaging apparatus 51 located within automatic drug packaging machine housing 27. Packaging apparatus 51 packages drugs 21 dispensed from cassettes 45 into separate packages 23 to generate the pouch package web 25. In the example, packaging apparatus 51 includes a roll (not shown) of the material used to generate the pouch package web 25. The material used for web 25 may be a lightweight low density polyethylene ("LDPE") film. The exemplary packaging apparatus 51 further comprises a hopper-like guide 53, a printer 55, and a sealer and perforation device 57. The operation of packaging apparatus 51 is carefully synchronized with operation of the cassette motor bases 47 to dispense and package drugs 21 in accordance with batch file information as described below so that the automatic drug packaging machine 11 can preferably produce any desired arrangement of pouch packages 23.

Referring to FIGS. 6 and 6A, drugs 21 dispensed in a singulated manner from the cassette 45 or other storage and dispensing apparatus may fall by means of gravity in the direction of the arrow through chutes (not shown) toward guide 53 of packaging apparatus 51. Guide 53 directs each drug 21 into the pouch package web 25. Guide 53 may include a counter 59 positioned in a path of drug 21 movement toward the pouch package web 25. Counter 59 may be a infra-red emitter and detector pair such as counter 49 provided on cassette base 47. Counter 59 registers a count each time a drug 21 passes counter 59 as the drug moves through guide 53.

The count generated by guide 53 counter 59 and the count from cassette base 47 counter 49 may be compared to the count required for the pouch package 23 to confirm that an identical quantity of each drug 21 dispensed from the cassette 45 has been loaded into the pouch package web 25 and that the counts from counters 49, 59 match the count required by the prescription order. This comparison of counts from counters 49, 59 is useful because drugs 21 can sometimes become lodged in the automatic drug packaging machine 11 and may not enter the pouch package web 25. A record of the counts from counters 49, 59 may be stored in a batch file associated with each pouch package 23. The batch file, including a subfile for each pouch package, may reside in a database in non-volatile memory 17 of computer 15. Each subfile may contain other information for the corresponding pouch package 23, examples of such information being described herein.

Referring further to FIG. 6, packaging apparatus 51 forms by folding a pocket 61 in pouch package web 25 as the web 25 is unwound from the supply roll (not shown). The pouch package web 25 is folded in half to form the pocket 61.

As illustrated in the example of FIG. 6, the web 25 may include a portion 63 which receives printed information thereon and a transparent portion 65. Once the pouch package 23 is formed in pouch package web 25, portion 63 becomes a first side 67 of pouch package 23 and the transparent portion 65 becomes a second side 69 of pouch package 23. Portion 63 preferably contrasts with printed information applied thereto and facilitates reading or machine detection (e.g., barcode recognition or optical character recognition) of the printed information. The transparent portion 65 permits each drug 21 to be easily viewed and imaged within each pouch package 23 for the purpose of creating an image record of the contents of each pouch package 23 as described herein.

In the example, the printer 55 shown schematically in FIG. 6, prints information on the folded web 25 portion 63 adjacent the location where each pouch package 23 will be formed before each drug 21 for a pouch package 23 is loaded into pocket 61 from guide 53. Another type of information-application device could be used in place of a printer 55. Advancement of the web 25 is stopped momentarily so that printer 55 may apply printed information 70 to the web 25 adjacent where each pouch package 23 will be formed in web 25.

Figure 16A:
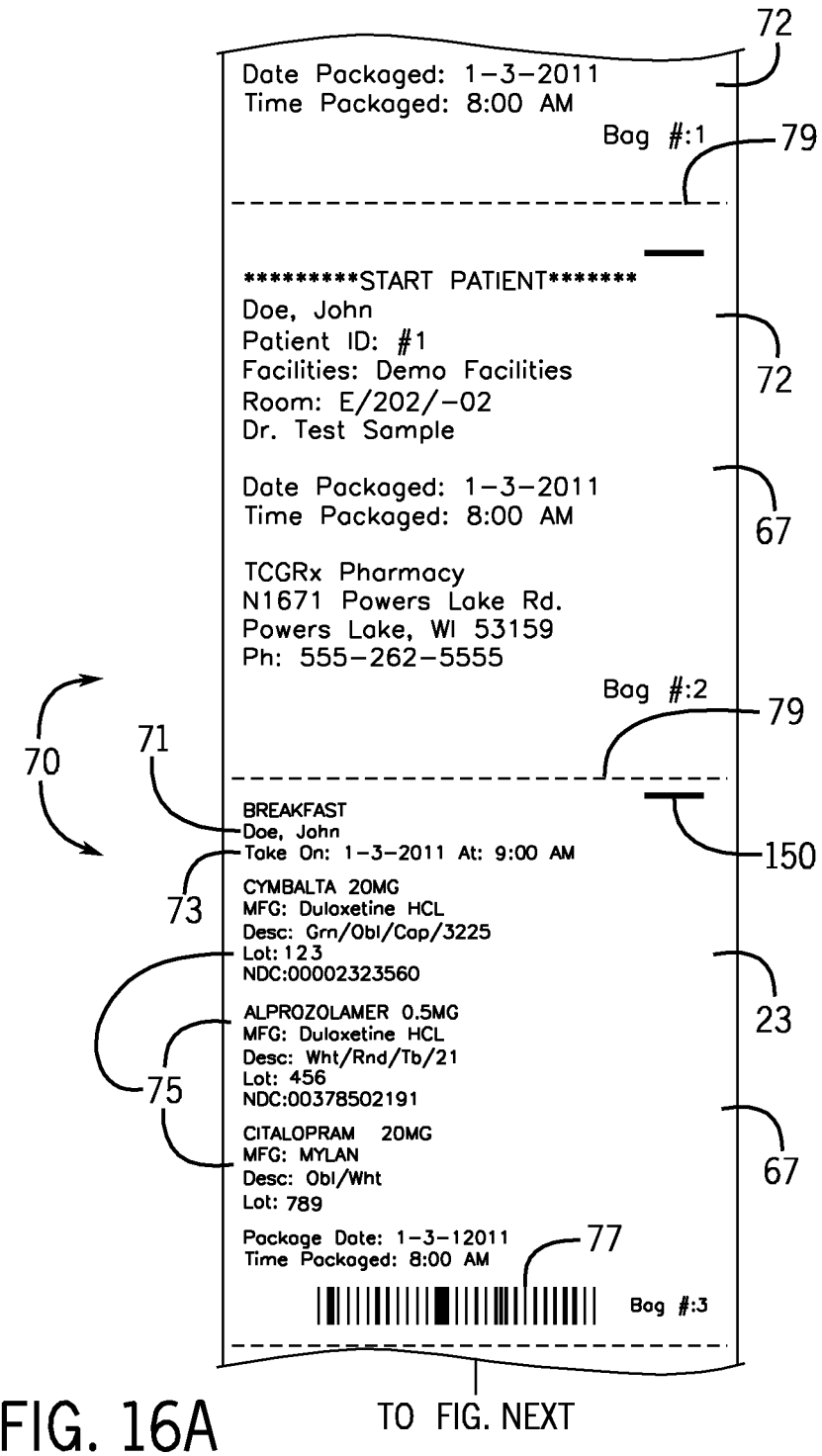
FIGS. 16A and 16B are enlarged views of portions of the exemplary pouch package web of FIG. 15A.
Figure 16B:
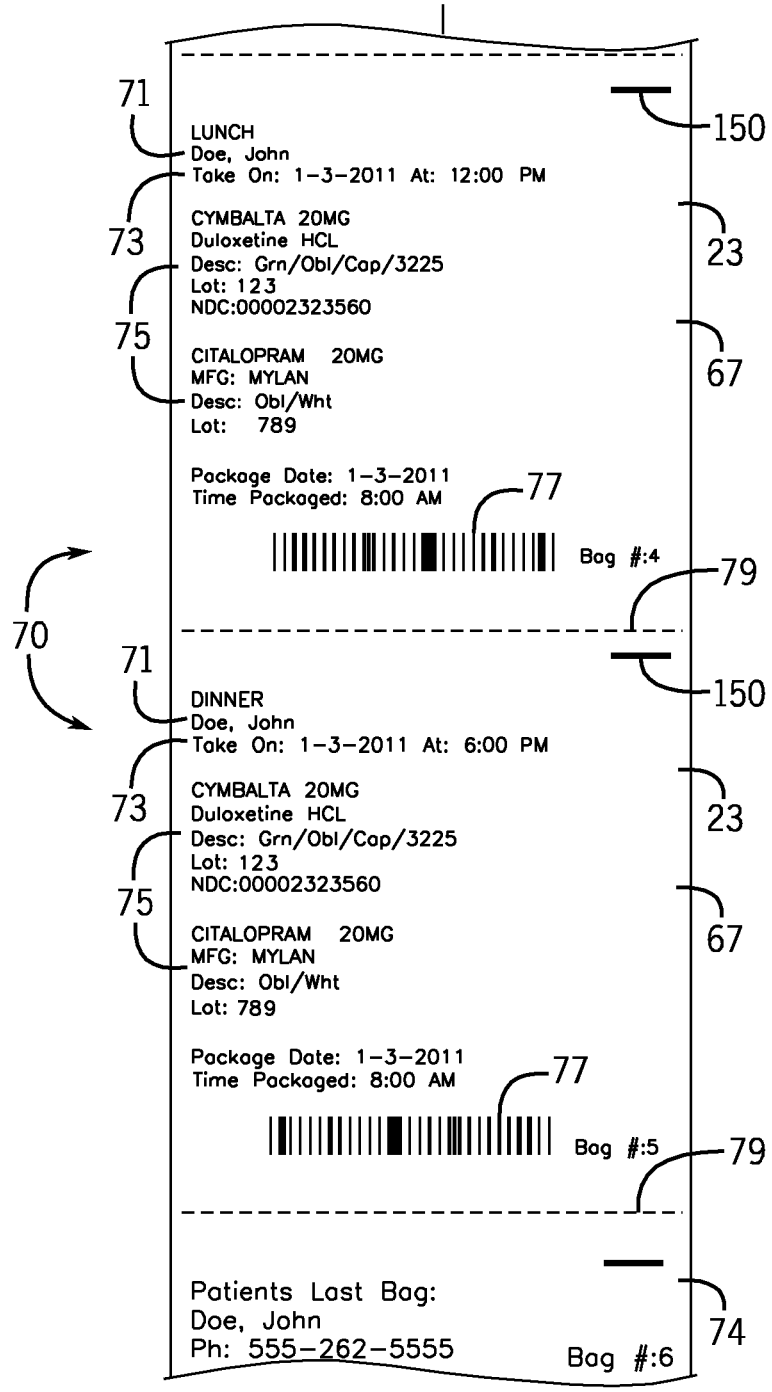
Figure 16C:
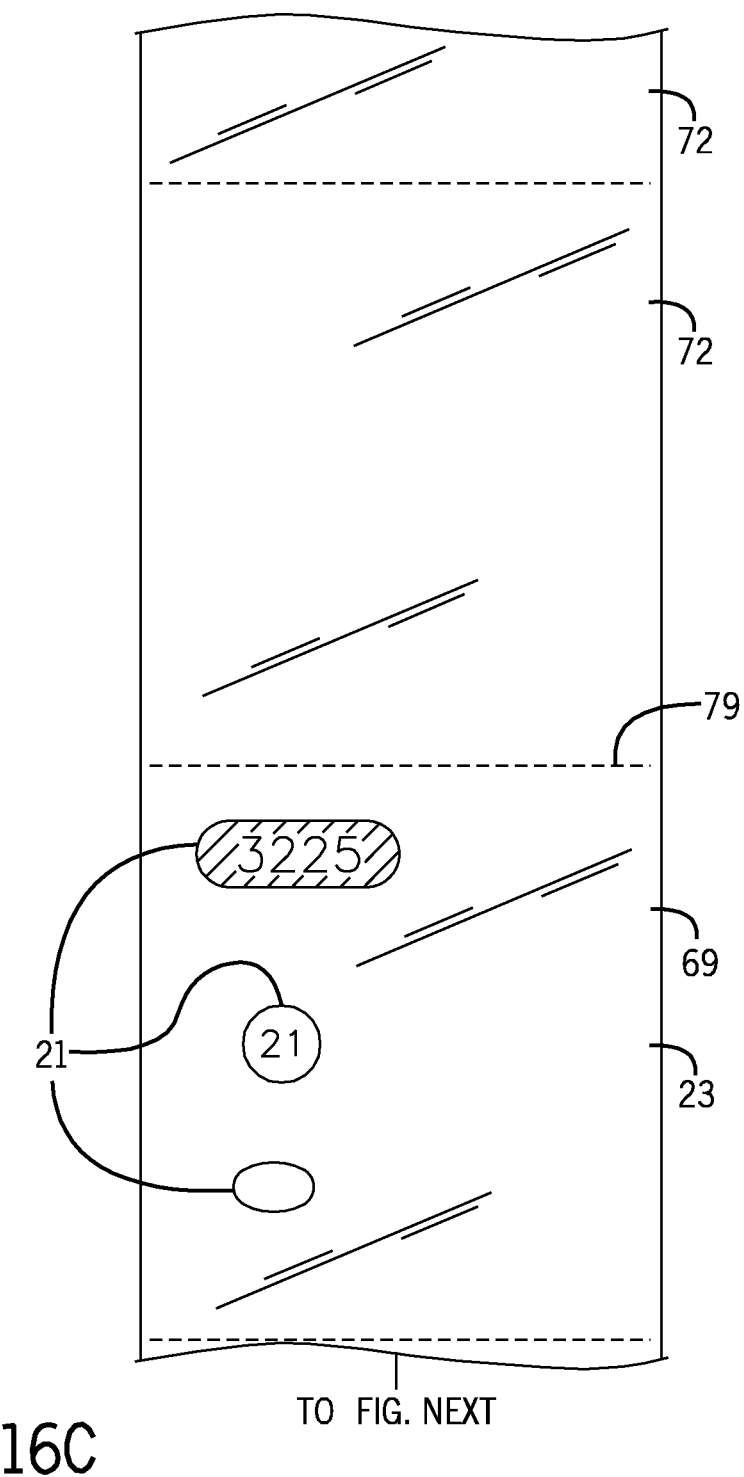
FIGS. 16C and 16D are enlarged views of portions of the exemplary pouch package web of FIG. 15B.
Figure 16D:
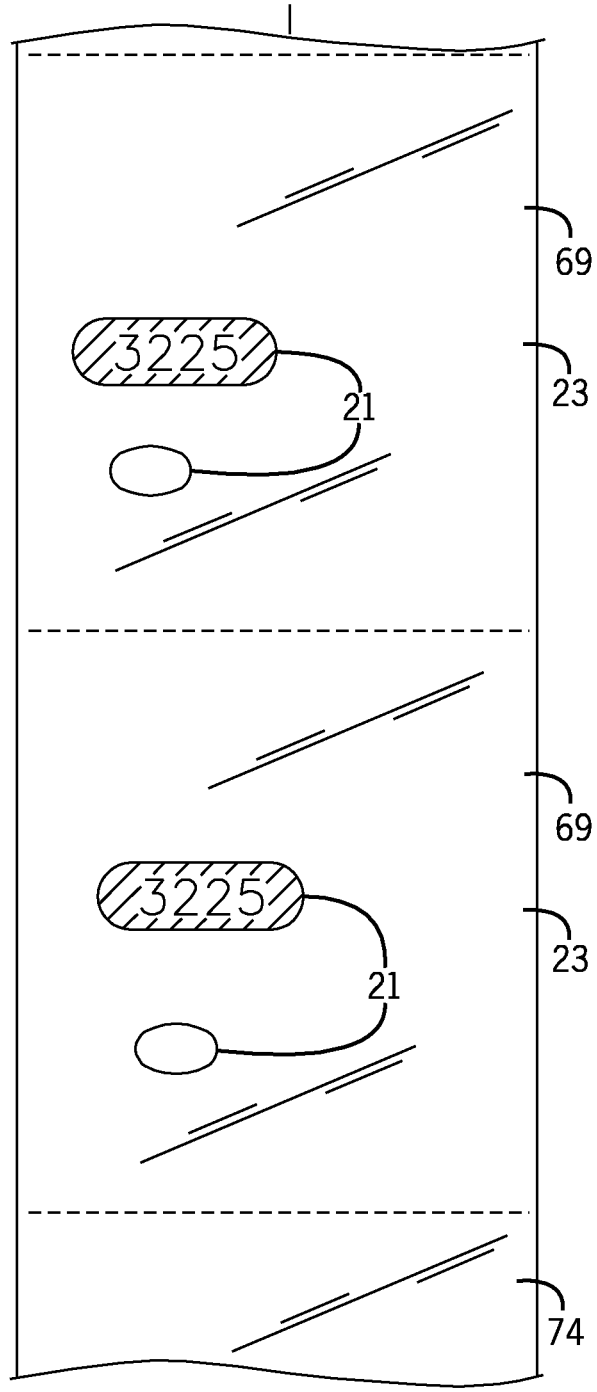
Figure 16E:
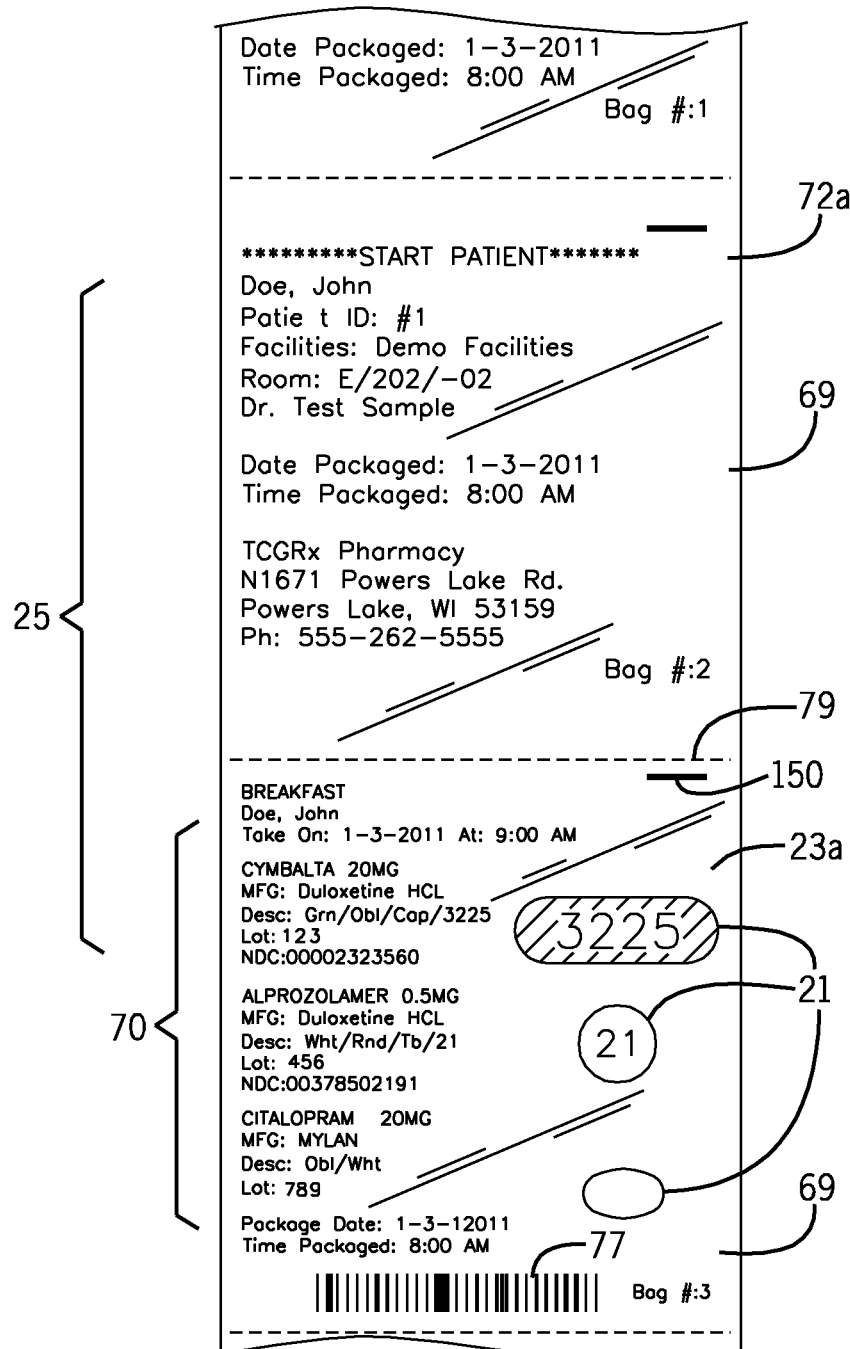
FIG. 16E is an enlarged view of a pouch package embodiment in which information is provided on a transparent side enabling simultaneous viewing of the information and drug.

As illustrated in FIGS. 16A, 16B, and 16E, printer 55, in synchronized operation with automatic drug packaging machine 11, may also print information 70 to provide an empty header package 72 (72a in FIG. 16E) indicative of the commencement of one or more pouch packages for a patient and information 70 to provide an empty trailing package 74 indicative of the end of the pouch package 23 for a patient. The header and trailing packages 72, 74 are useful to assist personnel in distinguishing the pouch packages 23 of one patient from the pouch packages 23 of another patient.

As illustrated in the example of FIGS. 15A, 16A, 16B, and 16E the information 70 applied to pouch package web 25 portion 63 may include any information deemed appropriate. The information 70 may include: the patient name 71, instructions for taking the drug 73 (e.g., date and time of day), drug information 75 (e.g., drug name, drug strength, drug appearance information, drug quantity, lot number, and expiration date), and a machine-readable code 77. Any combination of this information 70 or other information may be implemented by the pharmacy. The machine-readable code 77 may uniquely identify each pouch package 23. In the example, machine-readable code 77 is compared for a match with an expected code in a batch file subfile for the pouch package 23 for purposes of pouch package 23 verification as described below.

Figure 15A:
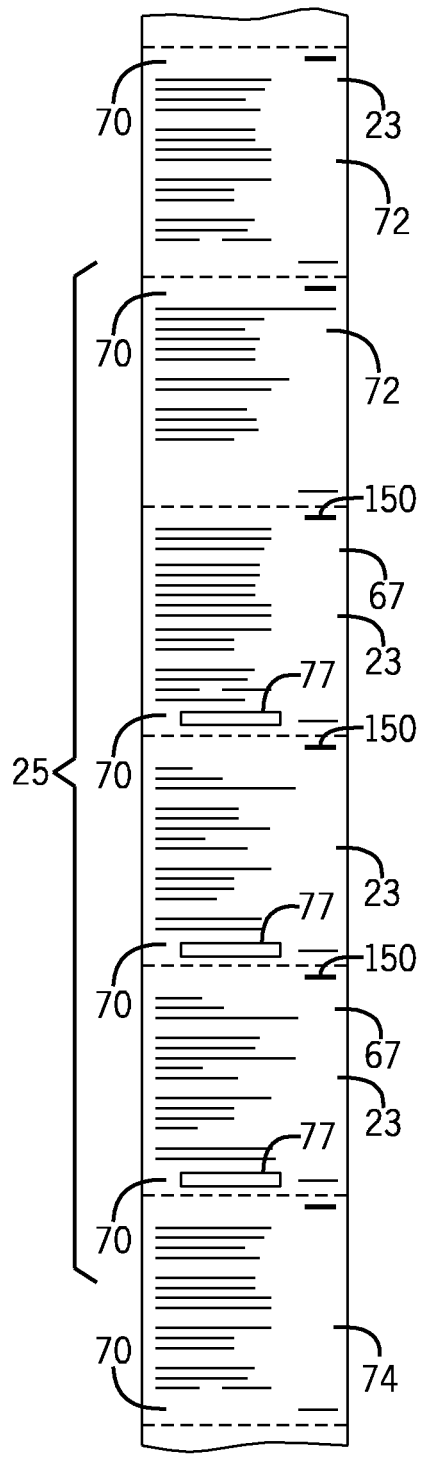
FIG. 15A is a top plan view of a first side of a portion of an exemplary pouch package web of a type output from the automatic drug packaging machine of FIGS. 1-5.
Figure 15B:
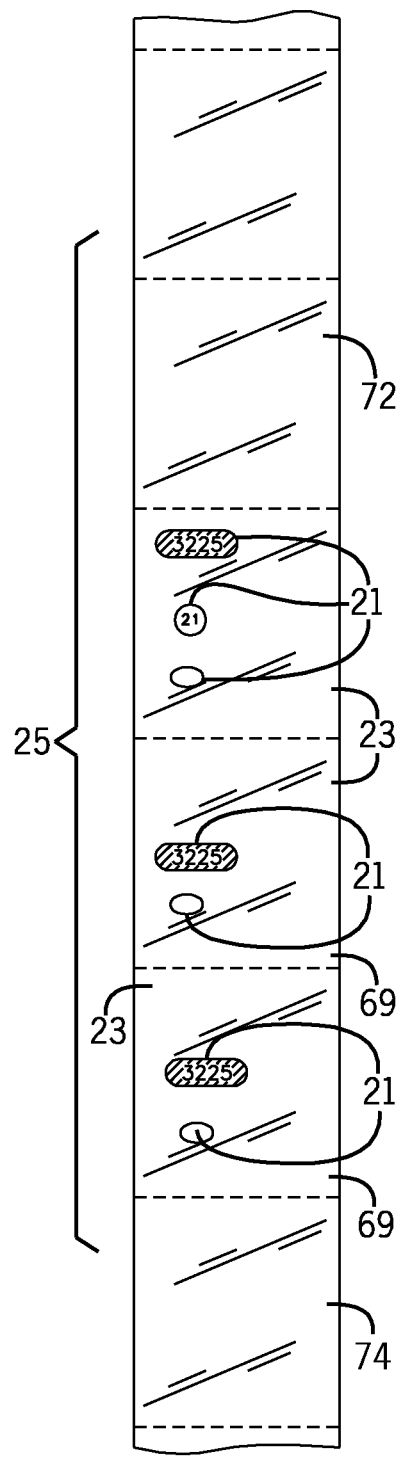
FIG. 15B is a top plan view of a second side of the portion of an exemplary pouch package web of FIG. 15A.

The machine-readable code 77 may be any suitable form of code. Each machine-readable code 77 illustrated in FIGS. 15A and 16B-16C is a barcode. If a barcode is selected as machine-readable code 77, the barcode may be of any format including, without limitation, Universal Product Code ("UPC"), Code 39, and PDF417. Other types of machine-readable code 77 may be utilized. For example, a radio frequency identification ("RFID") tag could be placed on or in each pouch package 23 to uniquely identify the pouch package 23. By way of further example, optical character recognition ("OCR") could be used in place of, or in addition to, a barcode or another form of machine-readable code 77.

In another embodiment illustrated in FIG. 16E, some or all of the information 70 may be on the transparent pouch package 23a second side. In this embodiment, printer 55 may apply some or all of the information 70 to the transparent portion 65 of pouch package web 25 during pouch package 23a generation. In such embodiments, the side 67 of pouch package web 25 preferably provides a background which clearly contrasts with the information 70 on pouch package 23a side 69 so that such information 70 can be easily read by a human or be capable of detection by a code reader or other device. By providing information 70 on the pouch package 23a transparent side 69, it would be possible to simultaneously view, or capture an image of, both the information 70 and appearance of each drug 21 on the same side of the pouch package 23a.

Referring again to FIG. 6, the packaging apparatus 51 fills, or loads, the drugs 21 into the pocket 61 formed in web 25 adjacent the corresponding printed information 70 (e.g., patient name 71, instructions 73, drug information 75, machine-readable code 77, etc.) on web 25. Guide 53 guides each drug 21 into pocket 61. Dispensing of each drug 21 from a cassette 45 (or other storage and dispensing apparatus) for each pouch package 23 and loading of each drug 21 into the pocket 61 is synchronized with printing by printer 55. At the same time that web 25 is momentarily stopped for printing, drugs 21 are loaded into pocket 61 downstream from printer 55 adjacent the corresponding printed information 70 (e.g., patient name 71, instructions 73, drug information 75, machine-readable code 77, etc.) for the pouch package 23 into which each drug 21 is loaded.

A sealer and perforator unit 57 shown schematically in FIG. 6, is used to seal each drug 21 into a discrete, separate pouch package 23 formed in the pouch package web 25. Sealer and perforator unit 57 may seal web 25 into separate pouch packages 23 by advancing web 25 between heated sealing rollers (not shown) or by other means, such as sonic welding. The sealer and perforator unit 57 may also perforate web 25 making a perforation line 79 between each adjacent pouch package 23 to permit each pouch package 23 to be easily separated from the pouch package web 25 by tearing. In embodiments, the automatic drug packaging machine 11 may be capable of generating a separate pouch package 23 approximately every one second.

Figure 16F:
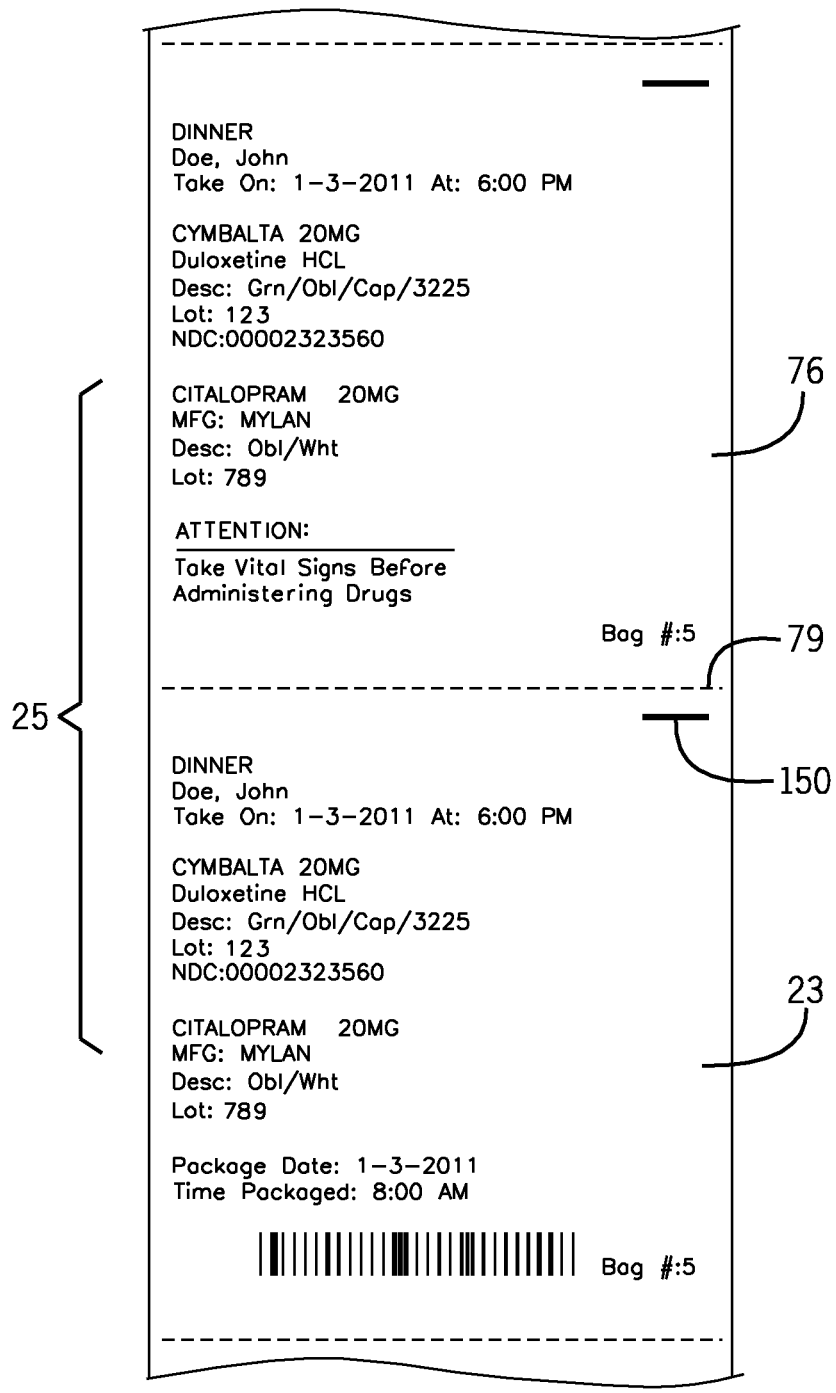
FIG. 16F is an enlarged view of a pouch package embodiment including a message package.

In addition to formation of pouch packages 23 and header and trailing packages 72, 74, automatic drug packaging machine 11 and packaging apparatus 51 may process web 25 in other manners. For example, and as shown in FIG. 16F, automatic packaging machine 11 and packaging apparatus 51 could provide a "message package" 76 in the pouch package web 25 for a series of pouch packages 23 for a patient. A message package 76 may comprise an empty package 76 between pouch packages 23. Information 70 useful to the patient or care giver may be provided on the message package 76.

Any information 70 useful to the patient or care giver may be provided on the message package 76. Information 70 may be provided from the patient's prescription order or any other source. As illustrated in the example of FIG. 16F, the information 70 provided on exemplary message package 76 advises the care giver to take the patient's vital signs before administering drugs 21 supplied in pouch package 23. By way of further example, the message package 76 may provide instructions to the patient for taking the drug 21 in the pouch package 23 adjacent to the message package 76.

Any number of message packages 76 may be provided. Preferably, the message packages 76 and information 70 thereon are created as part of the batch file containing the instructions used to operate automatic drug packaging machine 11 to package drugs 21 in the pouch packages 23.

After pouch package 23 formation and packaging, the pouch package web 25 is output through port 81 in automatic drug packaging machine 11 front wall 37. The port 81 is in communication with the package-less verification system 13 module 19. In the example, the package-less verification system 13 receives each pouch package 23 and performs the package-less verification as described below.

In summary, the exemplary product of the automatic drug packaging machine 11 comprises a pouch package web 25, or vine, of serially packaged pouch packages 23. Header, trailing and instruction packages 72, 74, 76 may be included. Each pouch package 23 contains at least one dose of a drug or drugs 21. Information 70 preferably provided by printer 55 may be on pouch package 23 first side 67 and each drug 21 in each pouch package 23 is easily viewable through the pouch package 23 second side 69. Alternatively, information 70 may be on second side 69 so that the information 70 and each drug 21 can be viewed simultaneously on the same pouch package 23. Each pouch package 23 of web 25 can be ordered in any appropriate manner and can be arranged serially by patient, or in the order in which the drug 21 doses are to be administered.

Verification System

Verification system 13 will now be described in connection with FIGS. 1-5 and 7-13A. The exemplary verification system 13 automatically provides verification that each drug 21 in each pouch package 23 is correct in accordance with a patient prescription order, or as otherwise required by the pharmacy. In the example, the verification system 13 implements a first package-less verification by means of code comparison and a second package-less verification by means of image comparison. The image comparison can be performed in real time as pouch packages 23 are packaged, or at a time subsequent to packaging of the pouch packages 23 utilizing stored image and other data for each pouch package 23. The verification processes provide for more complete assurance that the correct drug 21 has been provided to the patient in accordance with the patient's prescription order, thereby improving patient care. Further, the stored image and other data provide a record of proper packaging of each pouch package 23.

In the example, verification system 13 module 19 includes a housing 83 with top and bottom walls 85, 87 left and right sidewalls 89, 91, and a front 93 wall. Front wall 93 includes a port 123 through which pouch packaging material web 25 including pouch packages 23 is output from the automatic drug packaging and package-less verification system 10.

Module 19 may be attached to automatic drug packaging machine housing 27 by a piano hinge 94. Hinge 94 permits module 19 to swing to an open position shown in FIG. 5 for maintenance or cleaning. Module 19 is a particularly convenient way to retrofit an automatic drug packaging machine 11 with a package-less verification system 13. It is expressly contemplated that the invention may be embodied solely as a package-less verification system 13 and methods of use of same.

An electronic door interlock (not shown) may optionally be provided to ensure that the module 19 housing 83 remains in the closed position shown in FIGS. 1-4 against automatic drug packaging machine front wall 37 during operation of the system 10. This avoids tearing or breaking of the web 25 of pouch packages 23 during operation.

Housing 83 of module 19 may be provided to enclose components of the verification system 13. In the example, components within housing include an imager 95 consisting of first and second imaging devices 97, 99, a code reader 101, lamps 103, 105, shroud 107, a web drive system 109, a servo motor controller 111 for control of web drive system 109 servo motors 120, 122, a power supply 112, a communications hub 114, and a terminal block 116. Power supply 112 provides electrical power to the imaging devices 97, 99 of imager 95, code reader 101, lamps 103, 105, servo motor controller 111, servo motors 122, 124, marking device 141 (or 141a) and any other electrical components. Communications hub 114 provides an interface by which imaging devices 97, 99 of imager 95, code reader 101, servo motor controller 111, and marking device 141 or 141a are in data-transmission relationship with computer 15. The program of instructions executed by computer 15 controls operation of these components. The data-transmission relationship between computer 15 and components 95, 97, 99, 101 and 111, 141, 141a may be provided in any suitable manner. A terminal block 116 may be provided in module 19 for purposes of making electrical connections among the aforementioned verification system 13 components.

Referring to FIGS. 7-13A, imager 95 may be provided adjacent web path 110 to capture an image of each pouch package side 67, 69 to thereby create an image record of the pouch package 23 at the point of packaging by automatic drug packaging machine 11. While imager 95 is illustrated with two imaging devices 97, 99, it should be understood that any suitable type or number of devices may be provided to create the image record of the pouch package 23 at the point of packaging. In the example, imaging device 97 may be provided to capture an image 169 of the pouch package first side 67 and any information 70 thereon (e.g., patient name 71, instructions 73, drug information 75, machine-readable code 77, etc.) and imaging device 99 may be provided to capture an image 171 of the pouch package 23 transparent second side 69 so as to create a record of each drug in the pouch package 23. The image data corresponding to each image are transmitted to computer 15 via communications hub 114 for storage in the batch file subfile corresponding to the pouch package 23.

In a further embodiment, imager 95 may include one operating imaging device 99. Such an arrangement could be utilized with a pouch package 23a of the type previously described in connection with FIG. 16E wherein the information 70 and drugs 21 can be simultaneously viewed through one side 69 of the pouch package 23a. In such an arrangement, a single imaging device would capture the image 171. Imaging device 97 would not be necessary in this example. Imaging device 97 may be provided in such an embodiment, but may be disabled for use of verification system 13 with the type of pouch package 23a illustrated in FIG. 16E.

Imaging devices 97, 99 may each be a charged coupled device ("CCD"). The preferred CCD captures light and converts it to digital data that is stored through processing in each subfile for each pouch package 23 by computer 15. It is preferred that each imaging device 97, 99 has a resolution of about 4 to 8 Megapixels. Each imaging device 97, 99 is preferably cycled at a rate sufficient to gather the necessary image data 169, 171 (e.g., approximately 250 cycles/second).

Lamps 103, 105 may be any light source adequate for imaging of pouch packages 23 by imaging devices 97, 99. Lamps 103, 105 are supported by support structure 113 within module 19.

Code reader 101 is provided to read machine-readable code 77 on pouch package 23. In an embodiment, code reader 101 may be a barcode reader capable of automatically reading the barcode-type machine readable code 77. A barcode scanner or barcode reader is an apparatus which applies light such as a laser beam emitted from a light source toward a barcode portion and reads the barcode from an electronic signal obtained by receiving its reflected light. Barcode readers typically employ decoding circuitry to interpret the signals produced by a photodetector receiving the reflected light from the barcode symbol. Various types of bar code scanners are available including omni-directional scanners which use a series of straight or curved scanning lines of varying directions in the form of a starburst, a lissajous pattern, or other multi-angle arrangements which are projected at the barcode symbol assuring that the barcode is read at various orientations.

In another embodiment, code reader 101 may be a component integrated with imager 95 imaging device 97 or 99 capable of automatically reading the barcode-type machine readable code 77. As is known, camera-based barcode readers exist which utilize the camera to capture an image of a bar code. The barcode reader then uses sophisticated digital image processing techniques to decode the bar code. Camera systems incorporate robust decode software that reads 2D and linear bar codes on objects that are stationary or in motion. Decode software ensures the camera delivers the best possible read rates even on poor contrast bar codes. Interface targeting systems enable camera adjustments to accommodate changing production runs. The decoder can differentiate between codes in the camera's field of view or decode multiple codes simultaneously.

A support structure 113 within module 19 is provided to support imager 95 imaging devices 97, 99, code reader 101, and lamps 103, 105 with respect to the system 10. The exemplary support structure 113 may include mounts 117, 119, 121 secured directly or indirectly to support structure 113. Mounts 117, 119, 121 respectively support imaging devices 97, 99 and code reader 101 without any need for a human to hold a hand-held imaging device or code reader to perform the package-less verification. Referring to FIGS. 1-5 and 6-13, the support structure 113 supports imaging devices 97, 99 comprising imager 95 with their lenses and sensors facing one another. In the embodiment, imaging devices are positioned to image the pouch package first and second sides 67, 69 as web 25 is advanced between imaging devices 97, 99 during verification.

Web drive system 109 may optionally be provided to advance web 25 along a web guide 110 in synchronization with web 25 output from automatic drug packaging machine 11. Web drive system 109 advances web 25 between imaging devices 97, 99 from output of the web 25 through port 81 in front wall 37 of automatic drug packaging machine 11, through module 19 along guide 110 and out module port 123. Guide 110 may comprise an extrusion which partially supports web 25 for sliding across guide 110 as web 25 is advanced through module 19 by web drive system 109. In the example, guide 110 permits unobstructed imaging of pouch package 23 first and second sides 67, 69 by imaging devices 97, 99.

Figure 12:
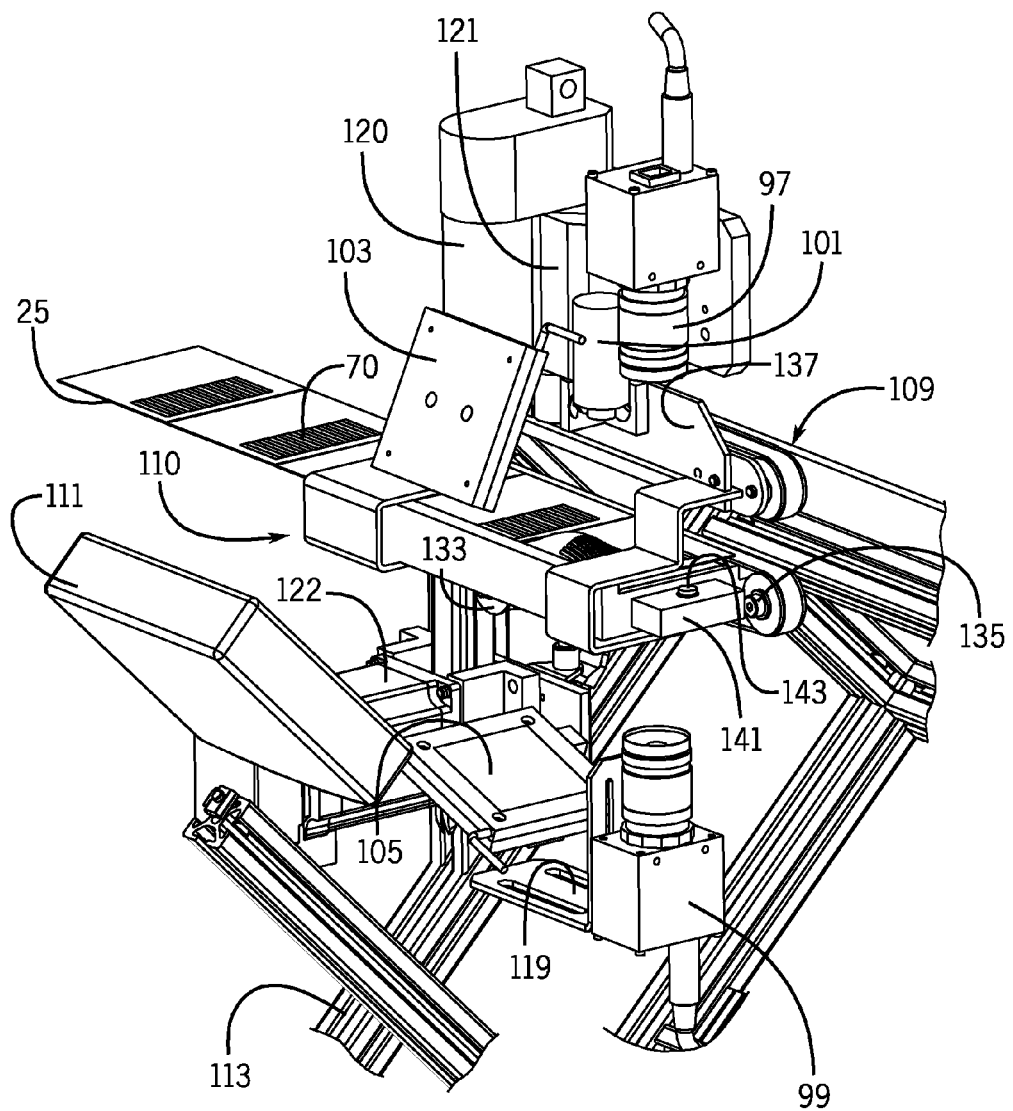
FIG. 12 is an enlarged fragmentary view of a code reader, an imager, a web guide and other components of the exemplary pouch package verification system module of FIGS. 1-5.

Drive system 109 includes a belt drive system with a first continuous belt 125 on idler rollers 127, 129 and a second continuous belt 131 on rollers, 133, 135 and a drive roller which is hidden in FIG. 12. The drive roller drives belt 131 and is driven by servo motor 122. A first servo motor 120 controlled by servo motor controller 111 powers one or both of rollers 133, 135 to synchronize advancement of web 25 with the packaging apparatus 51. Belts 125, 131 may form a nip which grips an edge portion of web 25. (FIGS. 7-13A show belts 125, 131 spaced apart for loading of web 25 on web guide 110.) Movement of powered belt 131 advances web 25 through module 19 along web guide 110.

Figure 5:
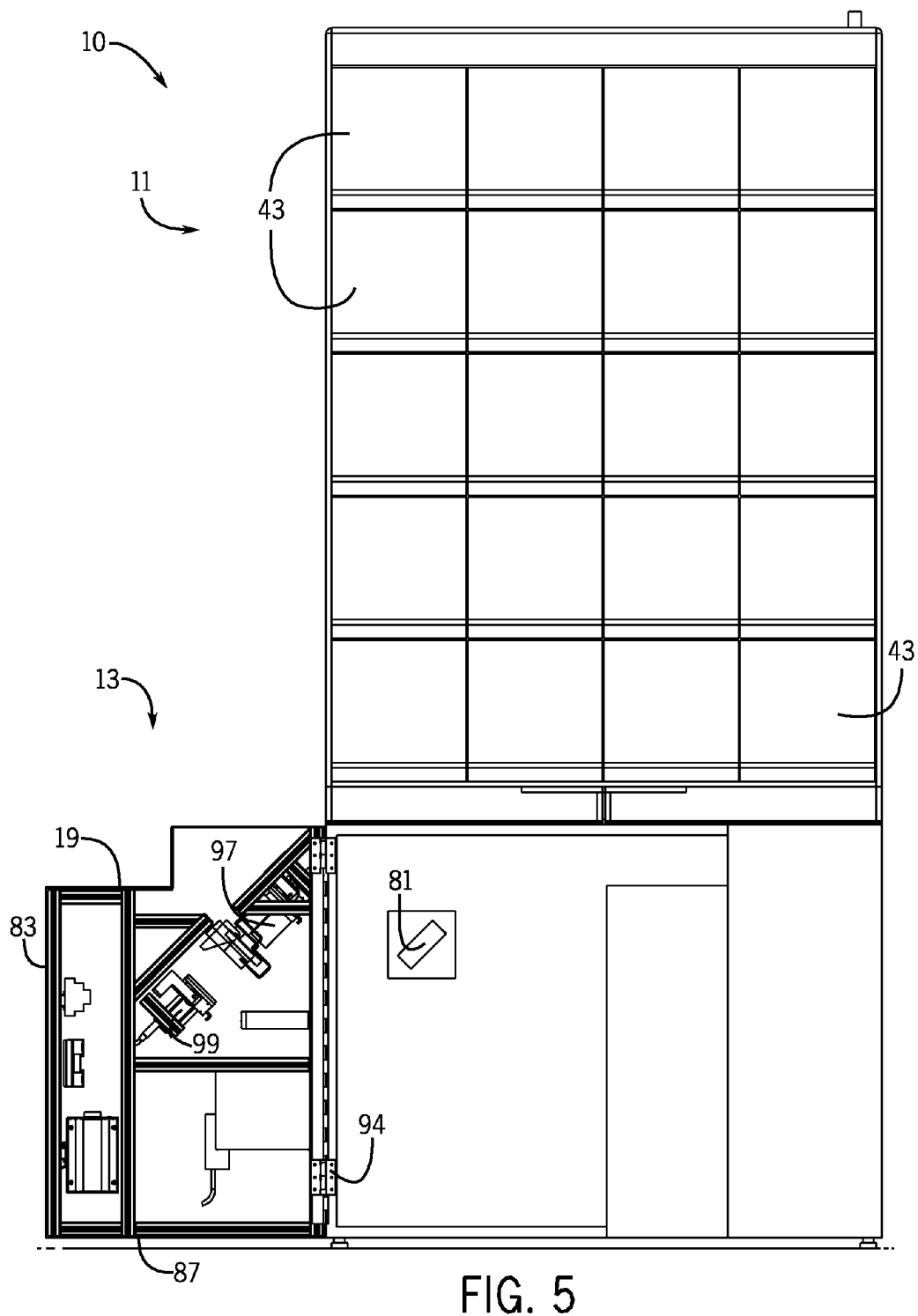
FIG. 5 is a front elevation view of the exemplary automatic drug packaging machine and package-less verification system of FIG. 1 but with a pouch package verification system module swung away from the automatic drug packaging machine.

Belt 125 may be moved toward and away from belt 131 to permit web 25 to be led between the belts 125, 131 on guide 110 when loading the web 25 into module 19 to begin verification of a batch of pouch packages 23. And, separation of the belts 125, 131 releases the clamping force applied by the belts 125, 131, permitting module 19 to swing to the open position illustrated in FIG. 5 without tearing web 25. The foregoing belt separation may be accomplished by mounting belt 125 rollers 127, 129 on a mount 137 which is capable of movement toward and, alternatively, away from web 25 and belt 131 in the directions of dual headed arrow 139. Servo motor controller 111 controls a second servo motor 122 to move mount 137 alternatively in the directions of arrow 139. Controller 111 can automatically move mount 137 away from belt 131 to release the force applied to web 25 to prevent tearing of the web 25 when housing 83 is opened and swung away from front wall 37 as illustrated in FIG. 5.

Shroud 107 may be supported by support structure 113 within module 19 adjacent lamps 103, 105 to at least partially block and reflect light from lamps 103, 105 to prevent unwanted light migration from module 19 and to better illuminate pouch package 23 first and second sides 67, 69 for image capture by imaging devices 97, 99.

Figure 13:
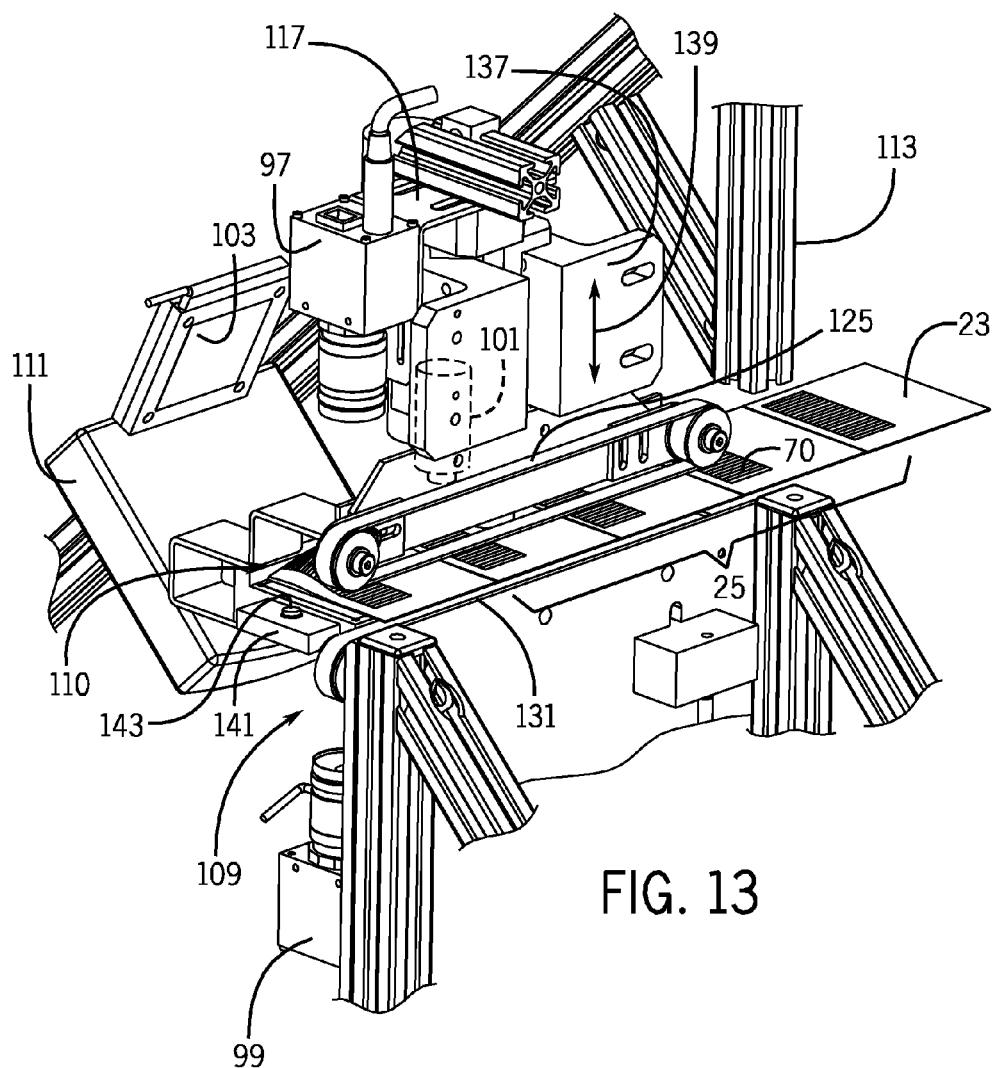
FIG. 13 is an enlarged fragmentary view of a code reader, an imager, a web guide and other components of the exemplary pouch package verification system module of FIGS. 1-5.
Figure 13A:
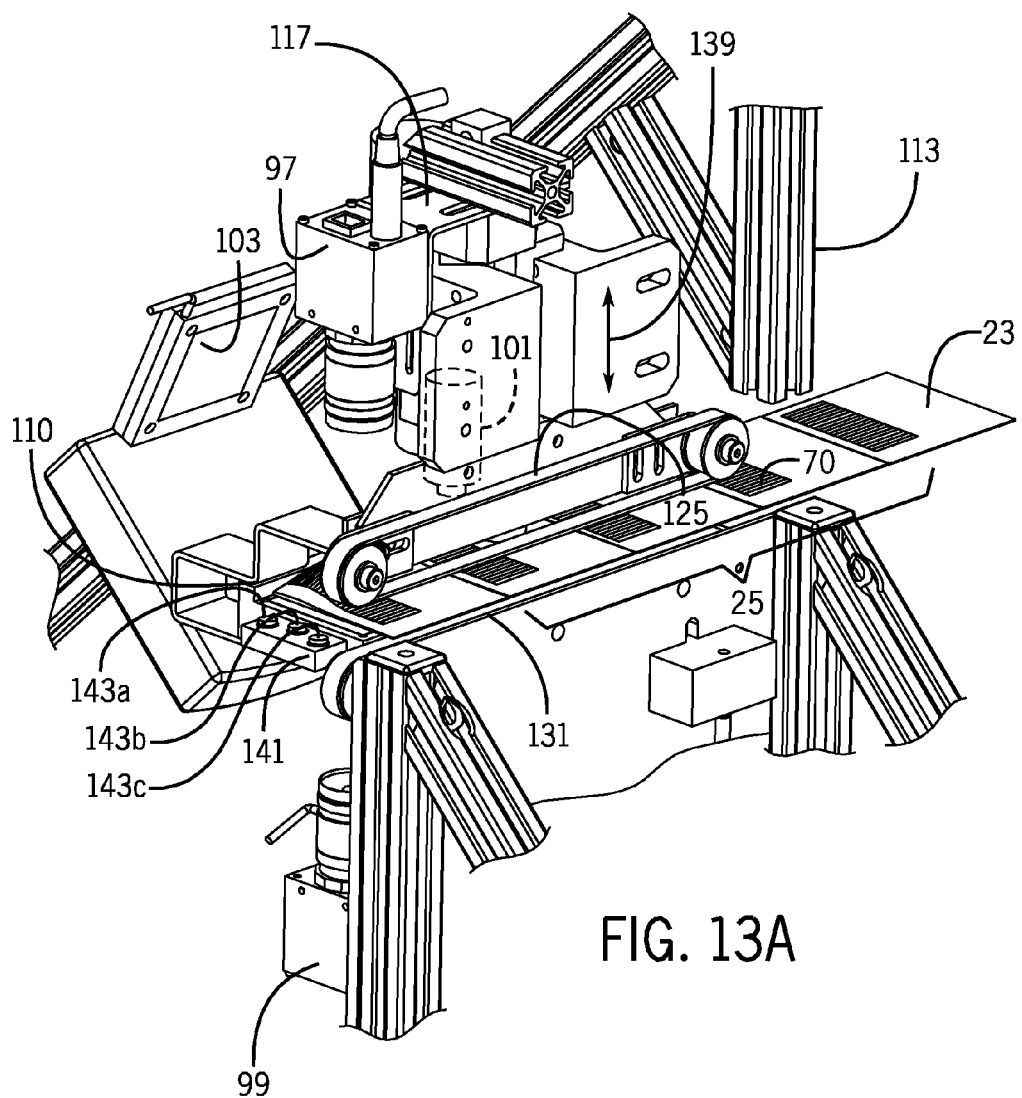
FIG. 13A is an enlarged fragmentary view of an alternative marking device embodiment and other components capable of use with the exemplary pouch package verification system module of FIGS. 1-5.

As illustrated in FIGS. 13 and 13A, a marking device 141 may be provided to place a mark (not shown) on each pouch package 23 determined to be potentially non-compliant at the time that the pouch package 23 is formed. The marking device 141 may include a marking tip 143 which extends to place the mark on the pouch package second side 69. The mark provided by the marking device 141 facilitates identification of the non-compliant pouch package 23 if it is necessary to retrieve the pouch package 23 from a group of look-alike pouch packages 23 in a pouch package web 25.

In an embodiment illustrated in FIG. 13A, a marking device 141a could be used in place of marking device 141. In the example, marking device 141a may apply more than one type of marking to a given pouch package 23. Marking device 141a is otherwise identical to marking device 141. Marking devices 141, 141a are preferably controlled by computer 15.

Marking device 141 or 141a could be utilized for purposes other than providing a marking indicating a non-compliant pouch package 23. For example, marking device 141a could be utilized to provide a classification code on the pouch package 23. A classification code may comprise a marking which provides some information or classification associated with the pouch package 23. For example, marking device 141a may be capable of applying more than one color to a pouch package 23 to color code the package 23. Marking device 141a could include any number of marking tips 143a, 143b, 143c with each tip capable of extension to apply a different color marking to a pouch package 23 under control of instructions executed by computer 15. The color coding may be set in the instructions for the pouch package 23 at the time of batch file generation. In the example, the classification code would be applied to the pouch package 23 as the pouch package web 25 is indexed along web guide 110 in contact with a marking tip or tips 143a, 143b, 143c.

By way of example, marking device 141a could be used to apply one color-type classification code (e.g., a green stripe) to a pouch package 23 intended to be administered at breakfast, another color-type classification code (e.g., a yellow stripe) to a pouch package 23 intended to be administered at lunch, and a further color-type classification code (e.g., a blue stripe) to a pouch package 23 intended to be administered at dinner. Application of a classification code to the pouch package 23 provides a further opportunity to improve the quality of patient care by assisting the patient to comply with a prescription order or other instructions.

Figure 2:
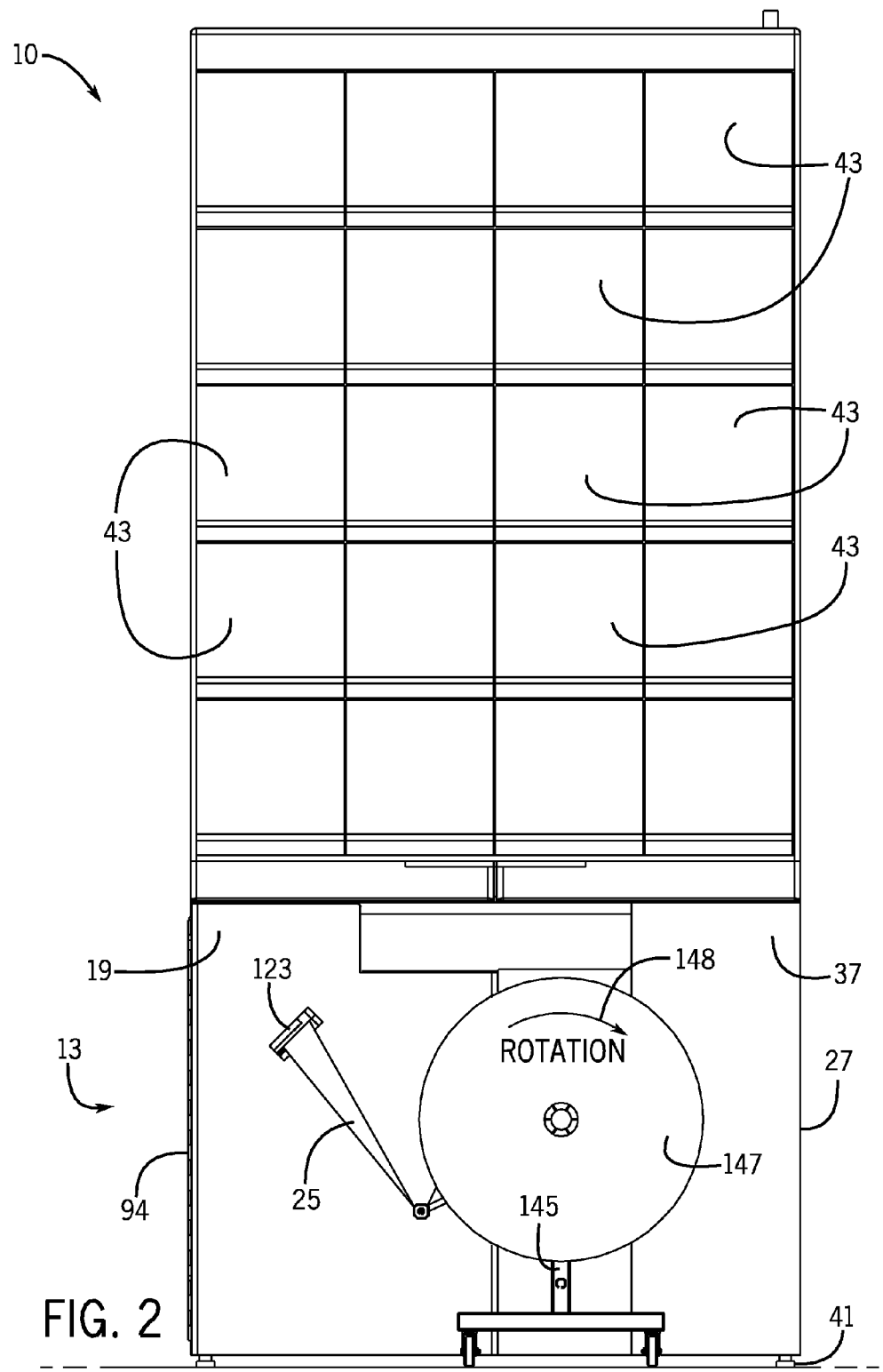
FIG. 2 is a front elevation view of the exemplary automatic drug packaging machine and package-less verification system of FIG. 1, together with a spooler for taking up a pouch package web output from the machine.

Upon exiting module 19 port 123, the pouch package web 25 may be taken up by a spooler 145 as illustrated in FIG. 2. Spooler 145 takes up the pouch package web 25 from automatic drug packaging machine 11 by winding the pouch package web 25 onto spool 147 in the direction of arrow 148. The spooler 145 provides a convenient alternative to allowing the pouch package web 25 to simply fall onto the floor or into a tote. Each spool 147 may be detached from spooler 145. As illustrated in FIG. 14, each loaded spool 147, including a length of pouch package web 25 wound thereon, may be placed on a rack 149. Rack 149 may be wheeled to an appropriate location for administration of the drugs 21 to each patient. Spoolers 145 are described in commonly-owned U.S. patent application Ser. No. 12/139,236, the contents of which are incorporated herein by reference.

If sold as a separate component, the package-less verification system 13 module 19 may be retrofit on a model ATP 128, 192, 256, 320, or 384 automated tablet packaging machine available from Chudy Group, LLC of Powers Lake, Wis.

Referring now to FIGS. 15A, 16A-16B and 16E-16F, a registration mark 150 may be provided to initiate image capture and reading of machine-readable code 77. Registration mark 150 may also facilitate complete image capture of the pouch package 23 and each drug 21 packaged in the pouch package 23, including for pouch packages 23 provided in different sizes.

The pouch packages 23 packaged by automatic drug packaging machine 11 and verified by verification system 13 may be provided in the pouch package web 25 in a single size or in different sizes. Different pouch package 23 sizes may be selected based on the quantity of drugs 21 to be packaged in each pouch package 23. The size of each pouch package 23 may be selected from a plurality of package sizes based on a setting in each subfile for each pouch package 23 upon creation of the batch file with instructions for loading each pouch package 23. By way of example, the pouch package 23 sizes may be small, medium, or large. Automatic drug packaging machine 11 controls printer 55 (or other information-application device) and movement of web 25 so that the printed or otherwise applied information 70 (e.g., patient name 71, instructions for taking the drug 73, drug information 75, and machine-readable code 77) is located approximately at the middle of the pouch package 23 for each of the small, or medium, or large package sizes.

As previously described, imager 95 imaging devices 97, 99 strobe continuously. Each strobe cycle represents a separate image. System 10 may be configured so that the only images of pouch package 23 first and second sides 67, 69 saved in each pouch package 23 subfile are the images 169, 171 in which the printed information on the first side 67 and second side 69 are properly centered for imaging devices 97, 99. Centering provides the opportunity to capture a complete image of the information on the first side 67 and drugs 21 viewable through the second side 69.

In order to identify to computer 15 which image to store in each subfile, a registration mark 150 may be provided as part of the printed information. The registration mark 150 is detectable by the first imaging device 97. The registration mark 150 is a marking or symbol which is recognized by the instructions residing in memory 17 of computer 15 for purpose of capturing the images with imaging devices 97, 99 when the information on pouch package 23 is properly centered in front of the first imaging device 97. Since second imaging device 99 faces first imaging device 97 and web 25, centering of first imaging device 97 on the printed information also centers the second imaging device 99 on the pouch package 23. The instructions executed by computer 15 capture the image of the pouch package first side 67 and, preferably, the image of the pouch package second side 69 responsive to detection of the registration mark 150. The instructions executed by computer 15 may further read the pouch package machine-readable code 77 with code reader 101 responsive to detection of the registration mark 150.

As illustrated in FIGS. 15A, 16A, 16B, 16E, 16F, and 17, the registration mark 150 may be a darkened rectangle located adjacent the printed information 70 including: patient name 71, instructions 73, drug type 75, and machine-readable code 77. As is apparent from FIGS. 15A, 16A, 16B, 16E, 16F, and 17, such information is generally centered on the first side 67 of each pouch package 23. The registration mark 150 appears in the same proximity to such printed information for each of the small, medium, or large size pouch packages 23.

In an embodiment, the instructions executed by computer 15 may be configured to save the images of the pouch package first and second sides 67, 69 generated at a preset time, or number of strobe cycles, responsive to detection of the registration mark 150 by imaging device 97. Each saved image 169, 171 of the pouch package first and second side 67, 69 is stored in the subfile for the pouch package 23. Consequently, the captured images of the pouch package first and second sides 67, 69 may always be generally centered on the pouch package 23 and a complete image record created and saved of such first and second sides 67, 69 for each of the different pouch package sizes (e.g., small, medium, or large pouch package sizes). The registration mark 150 can also be used in pouch package 23a embodiments such as shown in FIG. 16E in which the information 70 is on the transparent second side 69.

Exemplary Systems

Figure 17:
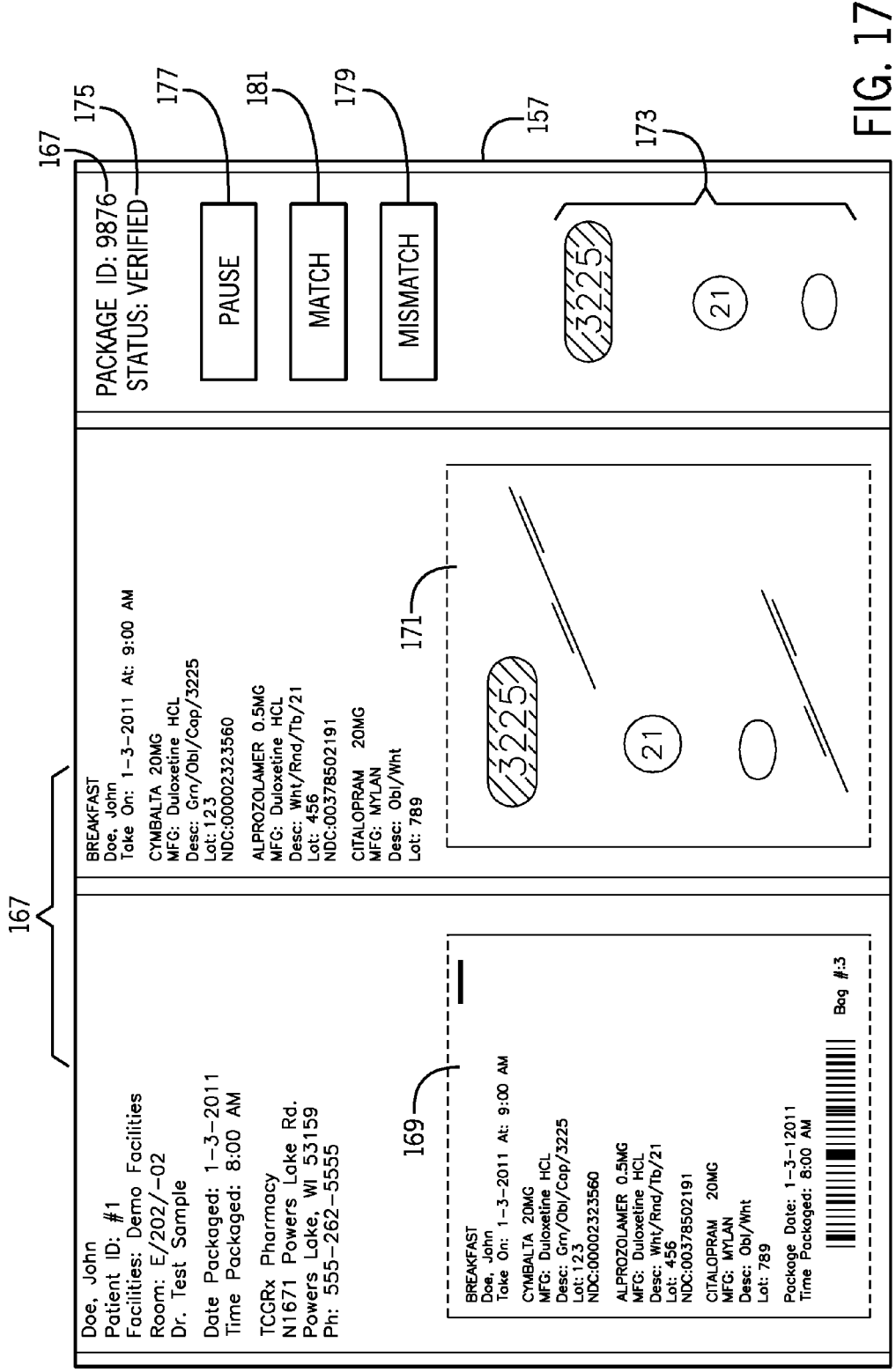
FIG. 17 is an exemplary verification workstation video display for a pouch package during verification.
Figure 18A:
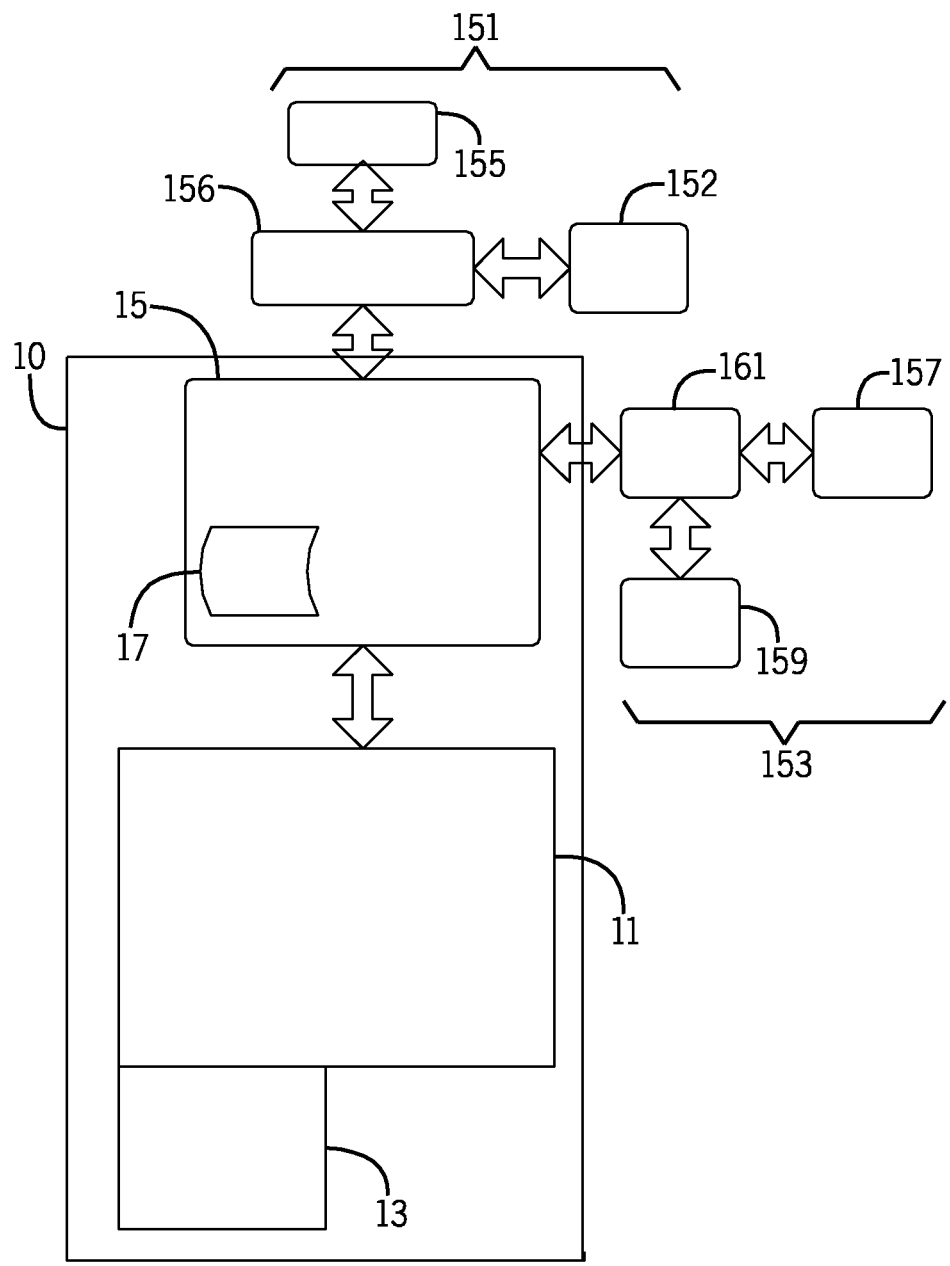
FIGS. 18A and 18B are block diagrams illustrating exemplary automatic drug packaging machine and package-less verification system embodiments.
Figure 18B:
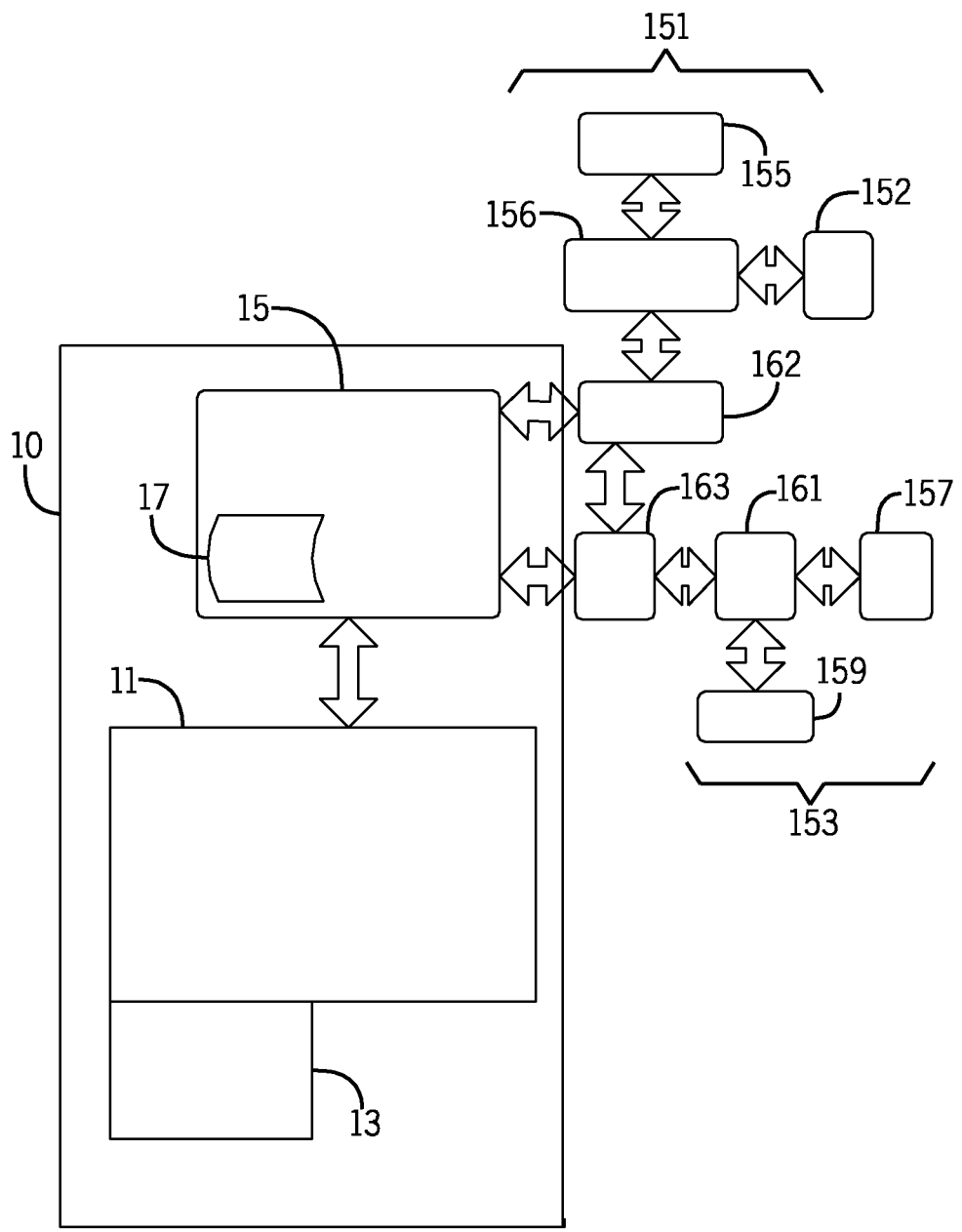

Referring now to FIGS. 17, 18A and 18B, those figures schematically illustrate that exemplary automatic drug packaging machine and package-less verification system 10 may interface with various workstations 151, 153 and components, such as video displays 152, 157 and input devices 155, 159. For example, a data entry workstation 151 and a verification workstation 153 may be provided. Data entry workstation 151 may include a video display 152 and one or more input device 155 for inputting information to a computer 156. Input device 155 may be one or more of a keyboard, a mouse, a touch screen video display, a code reader, or any other suitable device. Data entry workstation 151 may be provided for creation of batch files. Each batch file includes all instructions necessary to control operation of system 10 to package one or more pouch package 23, including any related packaging such as header or trailing packages 72, 74, message packages 76 and information 70 applied to such packages 23, 72, 74, 76. Preferably, each batch file has related subfiles that each include data relating to one pouch package 23, or header or trailing package 72, 74, or message package 76.

It will be understood that a file, batch file, or subfile are intended to be broad terms which mean or refer to one or more elements of data stored in memory which may be recalled by the system 10. It will be further understood that multiple memory locations may be utilized for storing the data elements relating to each file, batch file, or subfile. Therefore, the terms file, batch file, or subfile as used herein refer to the data elements for any given pouch package.

Verification workstation 153 may include a split screen touchscreen video display 157 (FIG. 17) and one or more input device 159 for inputting information to a computer 161 and to computer 15. Input device 159 may be one or more of a keyboard, a mouse, a touch screen video display, a code reader, or any other suitable device. Video display 157 displays generated data for a pouch package 23 to a user at workstation 153.

Data entry workstation 151 and verification workstation 153 may be connected to computer 15 for data transmission in any suitable manner such as by local area network ("LAN"), wide area network ("WAN"), by a pharmacy information system 162 used to control operation of the overall pharmacy, and by the Internet 163.

Verification workstation 153 may be co-located with system 10 or may be located at a location remote from (i.e., spaced from) system 10. And, verification workstation 153 could be both co-located with system 10 and located at a location remote from system 10. This arrangement permits pharmacist prescription order verification at virtually any location, including a location in a city or state far from the location at which system 10 packages the pouch packages 23. Further, this arrangement permits pharmacist prescription verification without the presence of the pouch package 23 at the first or second location and without the necessity that the pharmacist physically handle the pouch package 23.

Exemplary Operation

Operation of the exemplary automatic drug packaging machine and package-less verification system 10 will now be described in connection with the exemplary flow diagrams of FIGS. 19A and 19B. The exemplary process may include a first verification process and a second verification process. The first verification process preferably comprises an automatic code comparison at the point of packaging involving comparison of a code associated with a pouch package 23 and an expected code for the pouch package 23. The second verification process is preferably based on an image comparison of the pouch package 23 and its drug 21 contents against a reference image and other stored information for the pouch package 23.

The first and second verification process may occur in what is referred to herein as a "real time" verification mode in which both the first and second verification process occur at or shortly after each pouch package 23 is packaged by system 10. The second verification process may also occur in what is referred to herein as a "delayed time" verification mode in which the second verification process occurs at a point in time subsequent to the time that the pouch packages 23 are packaged by system 10. In the delayed time verification mode, the pouch packages 23 are packaged and the user relies on the information in each file for the pouch package 23 to perform the verification. Use of the terms real time and delayed time for the verification is done for convenience and is not intended to impose any particular limitations.

Both the first and second verification process may be considered "package-less" because the verification occurs without the necessity to physically handle or touch the drug 21 or pouch package 23 during the verification process.

In the example, the process is controlled by a program of instructions residing in computer 15 non-volatile memory 17. The process may be carried out by a computer program product, comprising a computer usable medium having a computer readable program code embodied therein. Execution of the computer readable program code would implement the process.

The process may be entered at Start 301 and includes a user login for continuing a data entry process. At block 303, a user creates a batch file at a data-entry workstation 151. The data entry workstation 151 may be directly or indirectly connected for data transmission to computer 15. A "user" of workstation 151 may be any of the pharmacy personnel authorized to enter data used to create the batch files. The batch files may be created from one or more prescription orders. The user at workstation 151 uses input device 155 for data entry of the batch files into a database. In this example, the database may reside in non-volatile memory 17 of computer 15. Persons of skill in the art will appreciate that the database of batch files may reside at any location on the network to which the system 10 may be connected for data transmission.

A batch file created in block 303 comprises a group of data elements that relate to a specific group of pouch packages 23. The batch file may further comprise a separate file containing a group of data elements that relate to each specific pouch package 23. The batch file may include any number of these separate files. For convenience, each separate file or data element relating to a specific pouch package 23 is referred to herein as a subfile. The batch file or subfiles may be supplemented with the data generated by the verification processes described herein to create a complete record of the packaging of each pouch package 23 and the status of the pouch package 23 as verified or non-verified. Data elements for each pouch package may be recalled from the batch file or subfiles for subsequent review and action as appropriate.

The data elements in each subfile include all information necessary to fully process each pouch package 23. These data elements may include the drug 21 to be packaged in the pouch package 23 and a unique code identifying the pouch package 23 and which matches fully or in part to the machine-readable code 77 which, in the example, is to be printed on the pouch package 23 first side. The data elements may further include the patient name, instructions for taking the drug (e.g., date and time of day), and drug information (e.g., drug name, drug strength, drug appearance information, drug quantity, lot number, and expiration date), as well as any other relevant information. The data elements may include other information needed including information for generation of the header, trailing, and message packages 72, 74, 76 and all information and instructions thereon. The data elements may include whether to place a color code on a pouch package 23 by means of marking device 141a. The data elements may also include package 23 size, for example, small, medium, or large size packages.

The subfiles within the batch file may be arranged in any manner. The subfiles may be organized to facilitate patient compliance with the physician's instructions as set forth in a prescription. To this end, the subfiles may be organized and arranged so that each pouch package 23 and the drug 21 in each pouch package 23 are in the order in which each drug 21 is to be taken. By way of further example, the subfiles may be organized in the order in which each drug 21 is to be administered to the patients within rooms of a hospital ward or long-term care facility ward. As yet a further example, the subfiles could be organized to serially load an identical drug 21 into a series of pouch packages 23.

At block 305, a user releases a batch file for processing by the automatic drug packaging machine 11 of system 10. (In FIG. 19A, automatic drug packaging machine 11 is referred to as "ATP") The computer 15 transmits the batch information to the automatic drug packaging machine 11. System 10 may be set in a real time verification mode or a delayed time verification mode.

At block 307, the automatic drug packaging machine 11 dispenses and packages each drug 21 required by a subfile. Printer 55 of the automatic drug packaging machine 11 prints any suitable information 70 on the pouch package web 25 preferably centered adjacent where the pouch package 23 will be formed. The information may include: the patient name 71, instructions for taking the drug 73 (e.g., date and time of day), drug information 75 (e.g., drug name, drug strength, drug appearance information, drug quantity, lot number, and expiration date), and machine-readable code 77. This information will preferably appear on the pouch package 23 first side 67, or second side 69, as previously described. Any classification code, such as color coding or other marking, may be applied by marking device 141a to the pouch package 23 at block 307.

As previously described, one or more drug 21 required by the subfile is dispensed from a cassette 45. Packaging apparatus 51 fills the pouch package web 25 with each drug 21. Sealer and perforator unit 57 seals the web 25 to form each discrete pouch package 23 and provides perforation line 79 in web 25 adjacent the pouch package 23. As appropriately sequenced by the batch file information relative to the pouch package 23, block 307 also results in sequenced generation of an empty header, trailing or message package 72, 74, 76 as previously described. Such packages 72, 74, 76 respectively indicate the beginning and end of a group of pouch packages 23 for a patient, and instructions or other useful information relating to the prescription order.

At block 309, the automatic drug packaging machine 11 packaging apparatus 51 indexes the pouch package web 25, to permit loading of the next pouch package, thereby elongating the pouch package web 25.

At decision point 311, the instructions executed by computer 15 determine whether a registration mark 150 indicative of a pouch package 23 has been detected by first imaging device 97 of imager 95. Imaging device 97 strobes at an appropriate rate to gather the necessary image data awaiting detection of the registration mark 150. Preferably, the registration mark 150 is positioned so that the pouch package 23 will be in proper position for complete first and second side 67, 69 imaging irrespective of the pouch package size (e.g., small, medium, large size) as previously described. The determination of registration mark 150 detection is made during each strobe cycle of imaging device 97 in the example. If no registration mark 150 is detected in a cycle, the process returns to block 307. The image captured in each cycle is not saved. If a registration mark 150 is detected in the cycle, the process advances to block 313. At block 313, the instructions executed by computer 15 in the example cause imager 95 first imaging device 97 adjacent the pouch package web 25 to capture an image of the information 70 on pouch package 23 first side (e.g., patient name 71, drug instructions 73, drug information 75, and machine-readable code 77) responsive to detection of the registration mark 150 at decision point 311. Detection of the registration mark 150 at decision point 311 also causes second imaging device 99 adjacent the pouch package web 25 to capture an image of each drug 21 within the pouch package 23 through the transparent pouch package second side 69. These two captured images are saved in the subfile for the pouch package 23 in the database which may reside in memory 17 of computer 15. If a pouch package 23a is used as in FIG. 16E and the information 70 and drug 21 are simultaneously viewed on a single package side 69, then only a single image 171 would be captured and stored in the pouch package subfile.

At block 315, the instructions executed by computer 15 cause code reader 101 to read, or capture, the machine-readable code 77 of the pouch package 23 responsive to detection of the registration mark 150 at decision point 311. Reading, or capturing, of the machine-readable code 77 preferably occurs simultaneously with image capture by imaging devices 97, 99. Therefore, if code reader 101 is a barcode reader and the machine readable code 77 is a barcode, the code reader 101 reads the barcode and the barcode is saved in the subfile for the pouch package 23 in the database which may reside in memory 17 of computer 15.

As a result of the exemplary actions at blocks 313 and 315, the images 169, 171 of the pouch package first and second sides 67, 69 and the code corresponding to the machine-readable code 77 are all associated with the subfile for the pouch package 23 in the database which may reside in memory 17 of computer 15. The subfile may be a part of the batch file including each other subfile. The subfile now includes data related to each drug 21 expected to be loaded into the pouch package 23, the code corresponding to the machine-readable code 77 and an image 169, 171 and machine-readable code 77 record of the pouch package 23 as output from the system 10.

First Verification Process

At decision point 317, the first pouch package 23 verification process is initiated. At decision point 317, the instructions executed by the computer 15 compare the code information in the pouch package 23 subfile for a match. The codes compared are preferably the code entered into the subfile at the time of batch file creation and the machine-readable code 77 actually read by the code reader 101. Data is generated responsive to whether the codes match. The data include at least a verification of the pouch package 23 if the codes match and, alternatively, a non-verification of the pouch package 23 if the codes do not match. The generated data may comprise a control signal which controls operation of system 10 responsive to whether the codes match. Because of the high degree of operational accuracy of automatic drug packaging machine 11, it is correct to conclude that if the machine-readable code 77 is verified as correct, then the other information 70 (e.g., patient information 71, drug instruction information 73, and drug information 75) on the pouch package 23 is correct and that each drug 21 in the pouch package 23 is also correct.

The comparing and data generation at decision point 317 may occur automatically after reading the pouch package machine-readable code at block 315. Preferably, the comparing and data generation occurs before the pouch package 23 exits the exemplary module 19 of the verification system 13.

Comparing and data generation as the pouch packages 23 are packaged, or shortly thereafter, provides immediate information to the pharmacy indicative of a potential error associated with the pouch package 23. This information provides the pharmacy with the opportunity to correct the error before a large number of potentially incorrect pouch packages 23 are processed. For example, a code mismatch could indicate the pouch package 23 is out of sequence and contains an incorrect drug 21. A code mismatch could also indicate a printer 55 malfunction, potentially rendering each pouch package 23 of the pouch package web 25, or vine, unusable. The pharmacist or pharmacy personnel is empowered to take steps to correct these problems.

At decision point 317, pouch packages 23 for which there is a code mismatch do not proceed to image verification. Pharmacy personnel are required to resolve the reason for the code mismatch in this example.

The instructions executed by computer 15 may create a record of the pouch package verification or non-verification based on the result of the code comparison at decision point 317. The record of the pouch package verification or non-verification is most preferably created in the subfile for the pouch package 23, thereby creating information in database residing in memory 17 that can later be recalled to confirm the contents of each pouch package 23.

Block 319 is entered to create a record if the code comparison at decision point 317 indicates there is no match and the status of the pouch package 23 is non-verified. Block 319 starts a process for resolution of the problem indicated by the code mismatch. The process provides immediate error detection so that the user can immediately take corrective action, thereby avoiding generation of an incorrectly-packaged web 25.

At block 319, the subfile for the pouch package 23 is updated to create a record of the mismatch and the occurrence is logged in the subfile by setting a non-verified state for the pouch package.

Also at block 319, information may be provided to the user to indicate the code mismatch at decision point 317. For example, the instructions executed by the computer 15 may be set to generate an audible or visual alarm if the codes do not match. The alarm would alert a user in real time of the potential error and enable the user to resolve the potential error, if desired.

At decision point 320, the instructions executed by computer 15 make a determination regarding whether the process is in the real time verification mode or the delayed time verification mode.

Decision point 321 is entered if the process is in the real time verification mode. At decision point 321, a determination is made regarding whether to immediately resolve the potential error indicated by the code mismatch at decision point 317.

Block 323 is entered if the result of decision point 321 is to immediately resolve the potential error. Resolution also involves providing a correct pouch package 23 for the prescription order if necessary so that the prescription order is correctly fulfilled. At block 323, the instructions executed by the computer 15 may be set to stop further operation of the automatic drug packaging machine 11 if the codes do not match. Stopping of the automatic drug packaging machine 11 would permit pharmacy personnel to resolve the potential error before proceeding with further packaging.

At block 325, actions are taken responsive to resolution of the code mismatch at block 323. At block 325, the subfile of the pouch package 23 is updated to create a record of the error and the occurrence is preferably logged in the subfile by indicating the nature of the potential error and resolution to create a record for the pouch package 23. The process for the real time verification mode proceeds to decision point 326 as described below.

Returning to decision point 321, if the process is in the real time mode (decision point 320) and the result of decision point 321 is to not immediately resolve the potential error or to take a further action responsive to the potential error, then the process moves to block 327. A "no" decision at decision point 321 represents a determination that the system 10 should continue to operate notwithstanding detection of the mismatch at decision point 317. The pharmacy will resolve the mismatch at a future time.

At block 327, actions may be taken to identify the non-verified pouch package for future corrective action. For example, the instructions executed by the computer 15 may be set to provide a modification of the pouch package 23 if the codes do not match. In an embodiment, the modification provided may be an identification mark made on the pouch package 23 by marking device 141. The identification mark applied to the pouch package 23 by marking device 141 indicates that the pouch package 23 may be incorrect and requires subsequent retrieval and attention before the drug 21 content can be administered to the patient.

As an alternative to marking (or in combination with marking), the instructions executed by computer 15 may be set to take other actions responsive to a code mismatch at decision point 317. For example, the instructions executed by the computer 15 may be set to modify the pouch package 23 in ways other than by marking. For example, the pouch package 23 could be modified in some physical and detectable manner by notching or cutting the pouch package 23 with a cutter or punch (not shown) for later identification and automated retrieval. The process for the real time verification mode proceeds to decision point 326 as described below.

Returning to decision point 320, if the instructions executed by the computer 15 determine that the process is in the delayed time verification mode (a "no" decision at decision point 320), the process immediately enters block 327 and carries out the steps to mark or otherwise identify the pouch package as described above in connection with block 327.

Decision point 326 is entered from block 325 for the real time verification mode and from block 327 for both the real time verification mode and delayed time verification mode in the example.

At decision point 326, the instructions executed by the computer 15 determine whether the pouch package 23 is the last file in the batch and whether additional pouch packages require packaging. If additional pouch package 23 subfiles of the batch file remain to be packaged, the process loops to block 309 and packaging by the automatic drug packaging machine 11 continues. If the pouch package subfile is the final subfile of the batch file at decision point 326, then the process proceeds to block 328.

At block 328 save log occurs and all data for the entire batch file is updated as saved in memory 17, including pouch packages which had a code match at decision point 317 and were subsequently verified as correct during image verification in the real time verification mode. A record is created of each pouch package 23 which is non-verified as a result of the code mismatch at decision point 317 together with the resolution of such mismatch.

At block 328, all data for pouch packages set for delayed time verification may be accessed as described in connection with FIG. 19B.

The process then ends at end point 330.

Returning to decision point 317, the result of decision point 317 if the code comparison is a match is that the subfile for the pouch package is verified as correct. The pouch package subfile may optionally be updated to create a record of the match and verification. Absence of a record of any mismatch is also indication in the subfile that the pouch package is verified as correct.

Second Verification Process

Figure 19A:
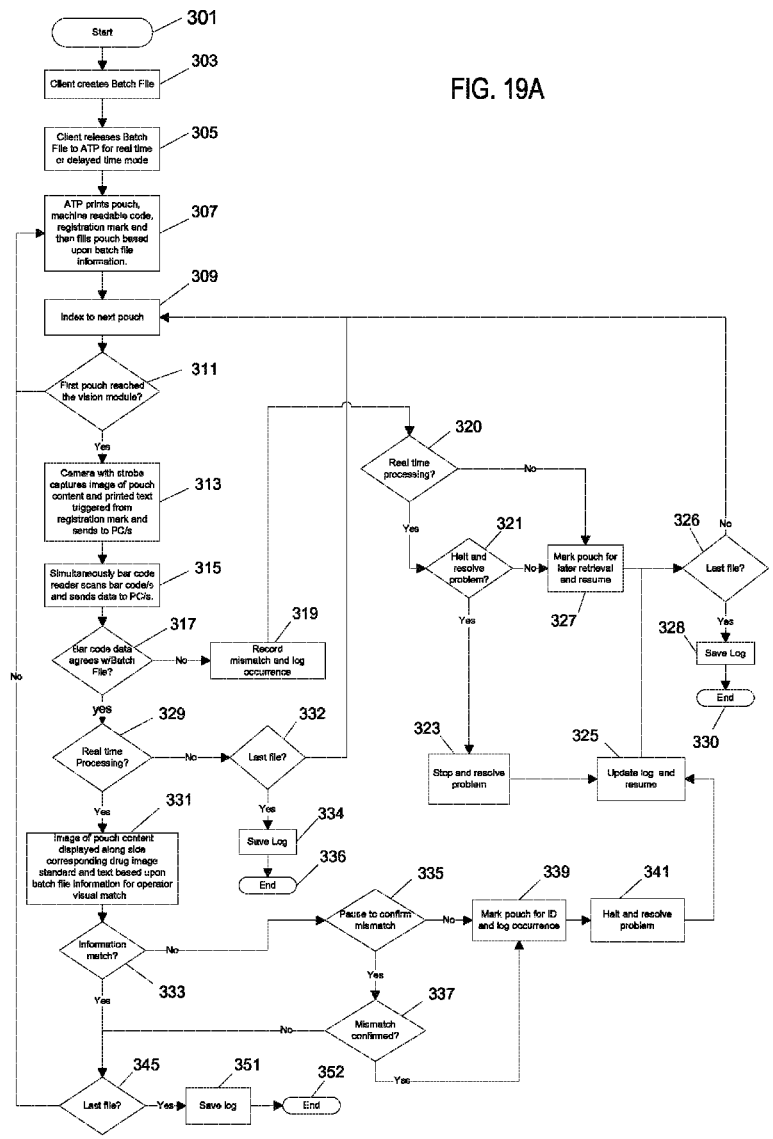
FIG. 19A is a flow diagram showing exemplary methods of real time package-less verification.

The second verification process may be entered at FIG. 19A decision point 329 for real time verification. The second verification process may separately be entered at FIG. 19B entry point 401 for the delayed time verification mode.

Referring then to decision point 329, the instructions executed by computer 15 make a determination regarding whether the process is in the real time verification mode or the delayed time verification mode. The process enters decision point 332 if the process is in the delayed time verification mode.

At decision point 332, if additional pouch package 23 subfiles of the batch file remain to be processed, the process loops to block 309 and packaging by the automatic drug packaging machine 11 continues. The process continues until all pouch packages of the batch have been packaged. If the pouch package subfile is the final subfile of the batch file at decision point 332, then the process proceeds to block 334.

At block 334 save log occurs and all data for the entire batch file is updated as saved in memory 17. The result of block 334 is that a record is created of each pouch package 23 which is verified as a result of the first verification and code match at decision point 317. All data for the batch file is now available for pharmacist image review and verification in the delayed time verification mode as described in connection with FIG. 19B. The process ends at 336.

"Real Time" Verification

Returning to FIG. 19A decision point 329, if the instructions executed by the computer 15 determine that the process is in the real time verification mode, the process enters block 331 for real time image verification. The real time verification occurs as the pouch packages 23 are packaged by system 10 immediately after decision points 317 and 319. In embodiments, the second image-based verification process could be performed in real time as each pouch package 23 is packaged and output by automatic drug packaging machine 11 and again at a subsequent point in time, for example as described in connection with FIG. 19B, if a further level of verification is desired.

Before commencement of the image verification process, the pharmacist must first login to computer 15 or a pharmacy information system 162 in data-transmission relationship with computer 15. The user may login with biometrics or password login with access granted based on the user security level. For example, a registered pharmacist would have the highest security level permitting the pharmacist to verify a prescription order while a pharmacy technician would have a lower security level permitting the technician to review pouch packages, but not verify a prescription order.

The image verification process may be performed at verification workstation 153 as previously described. As described in connection with FIGS. 18A and 18B, the workstation 153 may be at any user-designated location with workstation 153 in data-transmission relationship with computer 15, for example via an Internet 163 connection as represented in the example of FIG. 18B.

At block 331 and decision point 333 the second pouch package 23 verification process is initiated. In the example, this second pouch package 23 verification process comprises an image verification that the contents of the pouch package 23 are correct and fully in accordance with the prescription order or other instructions. As previously described, the second pouch package 23 verification process is package-less in the sense that it is based on review of saved data which may be in each subfile for each pouch package 23. The process frees the pharmacist or other user from the necessity to physically handle or touch the drug 21 or pouch package 23 during the verification process. This greatly improves verification accuracy and the rate of processing.

At block 331, the instructions executed by the computer 15 access the pouch package subfile and present generated data to the user on split screen touchscreen video display 157 as each pouch package is processed by system 10. FIG. 17 illustrates an exemplary screen display of display 157 during verification. The user may be simultaneously presented with generated data including: text information 167 from the pouch package subfile including the unique identification code for the pouch package, each drug 21 of the pouch package 23 and any prescription information for the pouch package 23, separate images 169, 171 of the pouch package first and second sides 67, 69, and a reference image 173 of each drug 21 which should have been loaded in the pouch package 23. One image of the pouch package 23 could be displayed if the text information and drug are visible through a single side 69 or of the pouch package 23.

The text information 167 may include data relating to the color, shape or marking on the drugs 21 expected to be in the pouch package 23. Such data may be provided in the subfile for the pouch package 23. The reference image 173 called for by information in the subfile also represents data relating to the color, shape or marking on the drugs because the reference image includes a graphic image of the physical appearance of the drug 21. The reference image 173 (three shown in FIG. 17) may be accessed over the Internet (e.g., Internet 163) or from a separate database. Commercial sources of reference image databases are First Databank of San Francisco, Calif. and Medispan of Indianapolis, Ind.

Information 175 may also be displayed on display 157 indicating whether the pouch package 23 is verified or non-verified based on the first verification process. Such verification or non-verification information 175 could be displayed on display 157 as, for example, text or as a green indicator for verification and a red indicator for non-verification. The user may then compare and verify all of the displayed information on video display 157 for the pouch package 23.

At decision point 333, the instructions executed by computer 15 provide for comparing of information generated at block 331 and a determination of whether the information matches. In the example, the instructions executed by computer 15 provide for comparing at least the image 171 of the drugs within the pouch package 23 and a reference image 173 of each drug 21 which should have been loaded in the pouch package 23. A pharmacist may make the determination of whether the displayed information matches. The pharmacist may, for example, push the match button 181 to indicate the match or may push the mismatch 179 button to indicate the result of the comparing. It is further envisioned that a computer may recall and compare the aforementioned data elements to make the same determination of whether the displayed information matches. Such computer comparison could occur at workstation 153 or elsewhere. This affirmative action of pushing the match buttons or mismatch buttons 181, 179 results in data generation for the pouch package 23 responsive to whether the comparison is a match or mismatch. The data generation includes a verification of the pouch package 23 based on the match and, alternatively, a non-verification of the pouch package if there is not a match.

The instructions executed by computer 15 may create a record of the pouch package verification or non-verification based on the result of the image comparison at decision point 333 (and the code comparison at decision point 317). The record of the pouch package verification or non-verification is most preferably created in the subfile for the pouch package 23, thereby creating information in a database residing in memory 17 that can later be recalled to confirm the contents of each pouch package 23. Absence of a mismatch record may be used to indicate that there was a match.

The process enters decision point 335 if the information does not match at decision point 333. At decision point 335, the user determines whether to pause the review and verification process to confirm the mismatch. The pharmacist or other user may push pause button 177 on touchscreen display 157 or otherwise operate a control to stop the automatic drug packaging machine 11 and verification system 13.

Decision point 337 is entered if the user elects to pause verification at decision point 335. At decision point 337, the instructions executed by computer 15 again provide for comparing of all or any portion of the aforementioned data and a determination of whether the displayed information matches. Like the comparing at decision point 333, the user (or a computer) confirms whether there is a mismatch of data displayed on video display 157. The pharmacist or other user may push the mismatch button 179 on touchscreen display 157 or otherwise operate a control to indicate the mismatch and non-verification. If there is a match, the user may push a match button 181 and the process continues to decision point 345. This affirmative action of pushing the mismatch or match buttons 179, 181 results in data generation for the pouch package 23 responsive to whether the comparison is a match or mismatch. The data generation includes a verification of the pouch package 23 based on the match and, alternatively, a non-verification of the pouch package if there is not a match.

Block 339 is entered if the mismatch is confirmed at decision point 337. At block 339, the instructions executed by the computer 15 may be set to provide a modification of the pouch package 23 if the codes do not match. In an embodiment, the modification provided may be an identification mark made on the pouch package 23 by marking device 141 or a physical change of the pouch package 23 which is detectable as previously described in connection with block 327 to indicate that the pouch package is potentially non-compliant and non-verified.

The result of an image mismatch at decision points 333, 335, and 337 and action in block 339, is to create an image-based record of the mismatch in the pouch package subfile for the pouch package 23 indicative that the pouch package is non-verified.

Block 341 is next entered for the real time verification process. In block 341 the instructions executed by the computer 15 may be set to stop further operation of the automatic drug packaging machine 11 so that the image mismatch may be resolved. Stopping of the automatic drug packaging machine 11 would permit pharmacy personnel to resolve the potential error before further pouch packages 23 are loaded, thereby avoiding creation of a pouch package web 25 with numerous incorrectly-packaged pouch packages 23.

Various options may be provided for creating a record of a non-verified and non-compliant pouch package 23. Upon identifying a non-compliant pouch package 23, a user may have the ability to flag and isolate by machine-readable code 77 that pouch package 23 for further review or for reference when removing the pouch package 23 from the pouch package web 25. The capability of flagging pouch packages 23 makes it possible to easily access all records for any pouch package 23 believed to be non-verified and non-compliant with the prescription order and to review all non-compliant pouch packages 23 at one time. Each subfile for each non-compliant pouch package may be updated to indicate the non-compliance.

Non-verified and non-compliant pouch packages 23 may optionally be put into a quality control review queue through, for example, a "Move to Q.C." button on display 157. The user may also have an option to select a "reason code" for any pouch package 23 determined to be non-verified and non-compliant and placed in the quality control queue. The quality control queue for each pouch package 23 may be updated by the user to indicate, for example, whether the printed information 70 (e.g., patient information 71, drug instruction information 73, drug information 75, machine-readable code 77) is illegible or incorrect, whether the drug 21 is not visible, whether the drug 21 is incorrect, whether the pouch package 23 is empty, and whether there is an under count or an over count.

The user may have the option to print a report of each pouch package in the quality control review queue. The report for each pouch package 23 may include, or not include, images 169, 171 of the pouch packages 23. Each pouch package 23 in the quality control queue may have associated with it the package first and second side 67, 69 images 169, 171, the reason code, a resolution code for the pouch package 23, the machine readable code 77 for the pouch package 23, the batch name, patient name, facility, and storage cabinet name.

"Resolution codes" may include: pouch verified, pouch modified, pouch destroyed or pouch destroyed and regenerated. There may be an option to sign off on all quality control resolved pouch package 23 by user name and by biometric user identification.

The data in the quality control review queue may be used to generate trending reports, exception reports and the like that can be used for diagnostic purposes, such as to identify excessive cassette 45 misfeeds involving over or under dispensing. The trending reports can be used to locate and replace potentially defective cassettes 45 or other components.

A record of flagged pouch packages 23 where a discrepancy was noticed can be used to re-generate replacement pouch packages 23 based on batch file information relating to the flagged pouch packages 23. This allows the flagged pouch packages to be removed from the spool 147 and replaced with replacement pouch packages while maintaining the correct total spool 147 count.

Block 325 is entered once the source of the potential error has been identified and resolved. At block 325, the subfile of the pouch package is logged and updated with the data saved in computer memory 17 to create a record of the mismatch and non-verification. The subfile may include text information entered by the user with input device (e.g., a keyboard or key pad on display 157) indicating the nature of the resolution.

Decision point 326 is entered after block 325. If additional pouch package 23 subfiles of the batch file remain to be processed, the process loops to block 309 and packaging by the automatic drug packaging machine 11 continues. If the pouch package 23 subfile is the final subfile of the batch file at decision point 326, then the process proceeds to block 328.

At block 328 save log occurs and all data for the entire batch file is updated as saved in memory 17. The result of block 328 is that pouch packages 23 have either been verified as correct by code and image verification or any non-verified pouch packages have been corrected and the pouch packages are ready for administration. The process ends at 330.

Returning to decision points 333 and 337, the user determines that the displayed information matches. At decision point 337 the user confirms whether there is a mismatch after pausing the system 10 for the verification process of the pouch package 23 being verified as previously described.

At decision point 333 the user determines that the displayed information in block 331 is correct for the pouch package 23. For both decision points 333 and 337, the user may push match button 181, or the like, to indicate the information has been compared and is correct and to update the subfile for the pouch package 23. This affirmative action results in data generation for the pouch package 23 responsive to whether the comparison is a match. The data generation includes a verification of the pouch package based on the match.

As an alternative, the pharmacist or other user could simply take no action at decision point 333, with the default condition being a match for the pouch package 23. This non-action also results in data generation for the pouch package 23 responsive to whether the comparison is a match.

The pouch package 23 subfiles are preferably updated throughout the process on a package by package basis to generate data. And, after each subfile of the batch file is complete, the batch file is then updated and saved, for example at block 351. The data generation includes a verification of the pouch package 23 based on the match. The result of successful image comparison in decision points 333, 337 is that the pouch package is verified as correct and in compliance with the prescription order. The pouch package 23 may subsequently be released for administration.

At decision point 345 a determination is made regarding whether the verified pouch package 23 is the final pouch package 23 of the batch file being verified. If there are other pouch packages 23 to be packaged as determined at decision point 345, the process loops to block 307 so that the next pouch package 23 can be packaged.

At block 351 save log occurs and all data for the entire batch file is updated as saved in memory 17. The result of block 328 is that pouch packages 23 have either been verified as correct by code and image verification or any non-verified pouch packages have been corrected and the pouch packages are ready for administration. The process ends at 352.

"Delayed Time" Verification

An exemplary delayed time image verification process will now be described in connection with FIG. 19B. The exemplary delayed time verification process provides the pharmacist or other user with the opportunity to package the pouch packages 23 at one time (for example, through completion of blocks 334 and 328 of FIG. 19A) and then to perform image review and verification of each pouch package 23 at any other time. By way of example, the delayed time verification process could occur one, two, or any number of days subsequent to output of the pouch packages 23 from automatic drug packaging machine 11 and completion of the first verification process based on the code comparison.

The second verification process may occur at workstation 153 as described in connection with the real time image verification mode. The workstation 153 can be at any location in data-transmission relationship with computer 15, or a like computer. All information for the delayed time verification may be in the subfile for each pouch package 23 saved during the first verification process. The pharmacist performs the review and verification using electronic records. There is no necessity that the pharmacist physically handle the pouch packages 23.

The process may be entered at Start 401. The pharmacist or user may login with biometrics or password login with access granted based on the user security level as previously described.

At block 403, the user first selects a batch or particular pouch packages for review and verification. The user may select a batch from a queue containing a plurality of batches awaiting image verification. The selection may be by any suitable manner including by touching a batch file displayed on touchscreen video display 157 or by scanning a code associated with the batch with a code-reader-type input device 159.

Selection of a batch accesses each subfile of the batch. The user may have the option to select for review the pouch packages based on any criterion such as: batch, patient, facility (e.g., hospital or long-term care facility, including by room, ward or other designation), by drug, or by pouch packages assigned to a medication cart or cabinet.

At block 405, and as with the real time verification, instructions executed by the computer 15 access a pouch package 23 subfile and present information to the user on the split screen touchscreen video display 157 at workstation 153.

At block 407, the information first presented to the user may be an indication of whether an error was detected during the first verification process ending at block 328 as indicated in the subfile for the pouch package 23. For example, a pouch package for which there was no code agreement could be identified to the user at block 407 for further attention, specifically to determine whether the pouch package 23 was properly packaged irrespective of the apparent code mismatch indicated at block 407.

At block 409, image information is presented to the user on display 157 to assist the user in understanding the source of the error indicated at decision point 407. At block 409, the instructions executed by computer 15 present generated data to the user on split screen touchscreen video display 157, preferably in the same manner as for the real time verification in block 331 and as illustrated in FIG. 17. The displayed information may include: the text information 167 and image information 169, 171 of the pouch package first and second sides 67, 69 from the subfile and reference image 173 of each drug 21 which should have been loaded in the pouch package 23. The verification status 175 of display 157 would indicate non-verified.

At decision point 411, the instructions executed by computer 15 provide for comparing of information generated at block 409 and a determination of whether the information matches. In the example, the instructions executed by computer 15 preferably provide for comparing at least the image 171 of the drugs within the pouch package 23 and a reference image 173 of each drug 21 which should have been loaded in the pouch package 23.

At decision point 411, the user examines the displayed information and compares the information indicating the expected content of the pouch package 23 and the information indicating what was actually packaged in the pouch package 23. The user determines whether the information matches. An information match is indicative that the error indication at decision point 407 is false. If the information does not match, then steps must be taken to resolve the problem.

Block 413 is entered if the information does not match at decision point 411. At block 413, the user resolves the problem. Resolution involves any step necessary to provide all pouch packages 23 required by the prescription order. Resolution may be simply updating the status of the pouch package 23 to indicate that the pouch package is verified as correct. Resolution may involve re-generating the pouch package 23 for packaging by system 10 so that the prescription order is complete. Resolution may further involve removal of any non-verified and non-compliant pouch package 23 from the pouch package web 25.

Block 415 is entered both if the result of decision point 411 is a match and after resolution of the problem in block 413. The purpose of block 415 is to create a record of resolution of the non-verification at decision point 407 (i.e., a code mismatch). At block 415, the pharmacist (indicated as "RPh" at block 415) creates a record in the pouch package 23 subfile that the pouch package 23 is correct and verified and indicates any other resolution of the verification error at decision point 407. Creation of such record in block 415 is desirable because the code mismatch at decision point 371 indicates that the pouch package 23 is non-verified and could contain a non-compliant drug 21. The data may be generated by means of text entered with input device 159 or by selection of a resolution code from a menu available on display 157.

At decision point 417, if additional pouch package 23 subfiles of the batch file remain to be processed, the process loops to block 419, the next subfile is accessed, and the process entered at decision point 407 is repeated until all pouch packages 23 of the batch have been verified or all problems resolved. If the pouch package subfile is the final subfile of the batch file at decision point 417, then the process proceeds to block 421.

Returning to decision point 407, if the pouch package 23 was verified as correct in the first verification process as indicated in the subfile for the pouch package 23, then the process moves to block 423.

At block 423, image information is presented to the user on display 157 so that the user can verify that the pouch package was packaged properly. At block 423, the instructions executed by computer 15 present generated data to the user on split screen touchscreen video display 157 in the same manner as for the real time verification in block 331 and as illustrated in FIG. 17. The displayed information 70 may include: the text information 167 and image information 169, 171 of the pouch package first and second sides 67, 69 from the subfile and reference image(s) 173 of each drug 21 which should have been loaded in the pouch package 23.

At decision point 425, the instructions executed by computer 15 provide for comparing of information generated at block 423 and a determination of whether the information matches. In the example, the instructions executed by computer 15 preferably provide for comparing at least the image 171 of the drugs within the pouch package 23 and a reference image 173 of each drug 21 which should have been loaded in the pouch package 23.

At decision point 425, the user examines the displayed information and compares the information indicating the expected content of the pouch package 23 and the information indicating what was actually packaged in the pouch package 23. The user determines whether the information matches. If the information does not match, the pharmacist or other user may push the mismatch button 179 on touchscreen display 157 or otherwise operate a control to indicate the mismatch and non-verification. The process then continues to block 413 for problem resolution as previously described. It is further envisioned that a computer may recall and compare the aforementioned data elements to make the same determination of whether the displayed information matches. Such computer comparison could occur at workstation 153 or elsewhere.

If there is a match at decision point 425, the user may push a match button 181 and the process continues to decision point 417. This affirmative action of pushing the mismatch or match buttons 179, 181 results in data generation for the pouch package 23 responsive to whether the comparison at decision point 425 is a match. The data generation includes a verification of the pouch package 23 based on the match and, alternatively, a non-verification of the pouch package 23 if there is not a match. The instructions executed by computer 15 may create a record of the pouch package verification or non-verification based on the result of the image comparison at decision point 423. The record of the pouch package verification or non-verification is most preferably created in the subfile for the pouch package 23, thereby creating information in database residing in memory 17 that can later be recalled to confirm the contents of each pouch package 23. Absence of a mismatch record may be used to indicate that there was a match.

The delayed time verification process is repeated through decision point 417 until all subfiles in the batch file have been verified as correct, or otherwise resolved.

Block 421 is entered through decision point 417 for the final subfile of the batch. At block 421 save log occurs and all data for the entire batch file is updated as saved in memory 17. All data for the batch file is now reviewed and verified by the pharmacist as correct or otherwise resolved in accordance with the prescription or other instructions. The process ends at 427.

Optionally, in an embodiment, a user may elect to perform only the first verification process initiated at decision point 317 without use of image verification. In such an embodiment, the user may only utilize a code comparison initiated at decision point 317 to determine whether the pouch package is verified or non-verified.

In a further embodiment, the user may elect to perform only the second verification process initiated at block 331 or start 401 in which the image information displayed on the video display 157 is compared for a match. Such image verification may be in real time verification mode or may be in delayed time verification mode as described above.

The automatic drug packaging machine and package-less verification system 10 described herein provides a full and complete record of each pouch package 23 and the content of each pouch package 23. The record preferably indicates whether the codes match and whether the images match. In the example, a verification of the pouch package may be indicated in the record if the comparisons match so that the pouch package can be administered to the patient with confidence that the prescription order has been correctly fulfilled. Alternatively, a non-verification of the pouch package may be indicated if either of the comparisons do not result in a match. This permits the pharmacist to withhold the pouch package from the patient and to take corrective action.

The record may be accessed any time it is necessary to establish that each pouch package 23 was properly packaged. For example, if a patient or care giver asserts that there was an undercount or incorrect drug in a pouch package 23, the subfile for that pouch package 23 can be accessed to demonstrate that the pouch package 23 was properly packaged. Such record would be quite valuable, particularly because of the complex nature of tracking the content of the many pouch packages 23 output from the automatic drug packaging machine 11.

The system 10 improves patient care by ensuring that prescription orders are fulfilled correctly. And, the system 10 has the potential to control healthcare costs by making the verification more efficient and by freeing pharmacists to assist patients and perform other tasks.

Point of Care Image Verification

FIG. 20 illustrates that the saved information in each subfile has uses other than to perform registered pharmacist prescription order review and verification. FIG. 20 illustrates that the information saved in each subfile for each pouch package 23 can be utilized for point of care (identified as "POC" in FIG. 20) verification prior to administration of a drug to a patient.

The process of FIG. 20 begins after a prescription order has been reviewed and verified as correct by the processes described herein, and has been released for prescription order fulfillment by a pharmacist. The process of FIG. 20 may be executed through components in data-transmission relationship with the database residing in memory 17 of computer 15, or a like database storing information for each pouch package 23 subfile.

The process is entered at start 501.

At block 503 a care giver, such as a nurse at a point of care, prepares to administer drugs to a patient. The point of care may be a hospital, a long term care facility, or any other location at which drugs 21 are administered to a patient. The care giver obtains packaged drugs 21, which may be packaged in pouch packages 23 as illustrated in FIGS. 15A-16F. The pouch packages 23 may be unwound from a spool 147 delivered to the point of care or otherwise received from a pharmacy or other source.

At block 505, the care giver scans a machine-readable code 77 on a pouch package 23 with a code reader. The machine readable code 77 may be a barcode as illustrated in FIGS. 16A-16B and 16E-16F and the code reader may be a barcode reader. A video display, such as display 157 of FIG. 17, or other display device is provided at the point of care. The barcode reader and video display are in data-transmission relationship with the database storing the subfile information for the scanned pouch package 23.

At block 507, image information is presented to the care giver on display 157, or another display device, so that the care giver can further confirm that the pouch package 23 was packaged properly and is the proper drug 21 for the patient. At block 507, the instructions executed by computer 15, or a like device, present generated data to the care giver on split screen touchscreen video display 157 in the same manner as for the real time image verification in blocks 331, 409, and 423 of FIGS. 19A-19B and as illustrated in FIG. 17. The displayed information may include: the text information 167 and image information 169, 171 of the pouch package first and second sides 67, 69 from the subfile and reference image 173 of each drug 21 which should have been loaded in the pouch package 23.

At decision point 511, the care giver examines the displayed information and compares the information on the pouch package 23 in the care giver's possession and the information indicating what was actually packaged in the pouch package 23 as presented on the display. The care giver determines whether the information matches.

Block 513 is entered if the information does not match. If the information does not match, the care giver stops administration of the drug 21 and resolves the problem.

Block 515 represents an entry point for an optional verification process. At block 515, the care giver can scan a patient bar code worn, for example on the patient's wrist. The patient bar code may be entered into the subfile for each pouch package 23.

At decision point 517, the instructions executed by computer 15 determine whether the patient bar code matches the code in the subfile. A code match at decision point 517 indicates that the pouch package is properly matched to the patient.

At block 519, the care giver stops the administration process if the codes do not match. A code mismatch could indicate that the pouch package 23 is not intended for the patient.

Block 521 is entered if the information matches at decision point 511 or at optional decision point 517. In block 521, the care giver accepts the drug for administration to the patient. The acceptance may be implemented by pushing a button, such as match button 181, on video display 157. The acceptance causes the information in the subfile to be updated in the database residing on, for example, computer 15 creating a record of acceptance in the subfile.

At block 523, the drug is administered to the patient.

The process ends at 525 with a successful verification of the drug 21 prior to administration to the patient.

The process described herein creates a record of the drug 21 administered to the patient and a record of further verification that the correct drug 21 in accordance with the prescription order was administered to the patient. The record may be accessed at a future point in time to confirm the drug 21 administered to the patient.

Reference to a computer program product or computer executable instructions may take any form capable of generating a signal, causing a signal to be generated, or causing execution of a program of machine-readable instructions on a digital processing apparatus. A computer program product or computer executable instructions may be embodied by a transmission line, a compact disk, digital-video disk, a magnetic tape, a Bernoulli drive, a magnetic disk, a punch card, flash memory, integrated circuits, or other digital processing apparatus memory device. Furthermore, the described features, structures, or characteristics of the invention may be combined in any suitable manner in one or more embodiments.

The steps shown in FIGS. 19A, 19B and 20 are described with respect to processes in the automatic drug packaging machine and drug verification system 10 of FIGS. 1-18. It will be apparent to one of ordinary skill in the art, however, that the method steps shown in FIGS. 19A-19B and 20, are applicable to distributed systems having a variety of configurations. The method shown in FIGS. 19A, 19B and 20, may also be performed by a process facilitating a service or performed by a separate process executed on a host, server or the like in a distributed system.

The apparatus, methods and computer code of the present invention may be performed by a computer program. The computer program can exist in a variety of forms both active and inactive. For example, the computer program can exist as software possessing program instructions or statements in source code, object code, executable code or other formats, firmware program(s), or hardware description language ("HDL") files. Any of the above can be embodied on a computer readable medium, which include storage devices and signals, in compressed or uncompressed form. Such computer readable storage devices include conventional computer RAM (random access memory), ROM (read only memory), EPROM (erasable, programmable ROM), EEPROM (electrically erasable, programmable ROM), magnetic or optical disks or tapes, firmware and similar storage modules. Computer readable signals, whether modulated using a carrier or not, can include heartbeat data packages, error data packages, test data packages and the like, all described above. It will be understood by those skilled in the art that a computer system hosting or running the computer program can be configured to access a variety of signals, including but not limited to signals downloaded through the Internet or other networks. Such may include distribution of executable software program(s) over a network, distribution of computer programs on a CD or DVD ROM, through firmware or through Internet download and the like.

The invention has been described with reference to preferred implementations thereof but it will be appreciated that variations and modifications within the scope of the invention will be suggested to those skilled in the art. For example, the invention may be implemented on networks including ethernet, token ring and the like or used to control other aspects of a system. The apparatus, methods and computer code of the present invention may be extended to monitor other devices which exhibit a plurality of operational modes.

Those skilled in the art will recognize that the techniques and embodiments described herein may be implemented with desirable results in all types of database systems. It is to be understood that several of the steps disclosed in the flow charts of FIGS. 19A, 19B and 20, including but not limited to the adjustment of the circuit parameters or timing, could be performed by software, firmware or the like programmed to carry out such steps. These steps could be performed, by way of example only, through software, firmware or a program storage device which may be part of a digital computer or computer network. In accordance with the present invention, the program or storage device may be implemented by a processor within a computer that executes a series of computer-executable instructions. These instructions may reside, for example, in RAM, ROM or other storage media of the computer, firmware or the like. Alternatively, the instructions may be contained on a data storage medium, such as a computer CD, DVD, ROM, RAM, diskette, USB drives, flash drive devices, solid state devices and the like. Furthermore, the instructions may be stored on a DASD array, magnetic tape, conventional hard disk drive, electronic read-only memory, flash memory, USB drives, optical storage device, solid state drives, or other appropriate data storage device. In such alternate embodiments, the computer-executable instructions may be lines of compiled executable code as available in any computer executable code, steps or language.

Reference throughout this specification to "the embodiment," "this embodiment," "the previous embodiment," "one embodiment," "an embodiment," "a preferred embodiment," "another preferred embodiment," or similar language means that a particular feature, structure, or characteristic described in connection with the embodiment is included in at least one embodiment of the present invention. Thus, appearances of the phrases "in the embodiment," "in this embodiment," "in the previous embodiment," "in one embodiment," "in an embodiment," "in a preferred embodiment," "in another preferred embodiment," and similar language throughout this specification may, but do not necessarily, all refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

While the present invention has been described in connection with certain exemplary or specific embodiments, it is to be understood that the invention is not limited to the disclosed embodiments, but, on the contrary, is intended to cover various modifications, alternatives, modifications and equivalent arrangements as will be apparent to those skilled in the art. Any such changes, modifications, alternatives, equivalents and the like may be made without departing from the spirit and scope of the invention.

What is claimed is:

1. An automatic drug packaging machine and package-less verification system, comprising:
   an automatic drug packaging machine including a support structure, an information-application device and a packaging apparatus within the automatic drug packaging machine for packaging one or more drug into ones of separate pouch packages one after the other thereby forming a pouch package web, each pouch package having sides including a side through which each packaged drug is viewable;
   an imager secured with respect to the support structure to capture an image of the pouch package during formation of the pouch package web;
   a code reader secured with respect to the support structure to read a machine-readable code applied by the information-application device to each pouch package during formation of the pouch package web; and
   a computer programmed with instructions for performing a method of package-less verification of the pouch packages including:

storing information in non-volatile memory for packaging of each pouch package, the stored information including an identification code for each pouch package;

applying the stored information to a side of the pouch package with the information-application device during formation of the pouch package web, the applied information including human-readable information and a machine-readable code corresponding to the identification code;

packaging a drug within the pouch package during formation of the pouch package web;

capturing an image of the pouch package including each packaged drug therein and the applied human-readable information during formation of the pouch package web;

storing the image of the pouch package including the images of each packaged drug therein and the applied human-readable information with the stored information for the pouch package during formation of the pouch package web;

reading the machine-readable code with the code reader during formation of the pouch package web;

comparing the machine-readable code of the pouch package with the stored identification code for a match during formation of the pouch package web;

displaying the stored image of the pouch package including the images of each packaged drug therein and the applied human-readable information thereby enabling a comparison of the displayed images with the stored information for the pouch package for a match; and creating a record for the pouch package during formation of the pouch package web responsive to whether the machine-readable code matches the stored identification code and creating a record for the pouch package responsive to whether the image of each packaged drug and the image of the applied human-readable information match the stored information for the pouch package, the pouch package being verified as correct if the comparisons match and, alternatively, being non-verified if at least one of the comparisons do not match.

2. The automatic drug packaging machine and package-less verification system of claim 1 wherein creating the record for the pouch package during formation of the pouch package web occurs automatically after reading the machine-readable code.

3. The automatic drug packaging machine and package-less verification system of claim 1 wherein the automatic drug packaging machine further comprises a module, the module includes the support structure, and the imager and code reader are secured to the support structure within the module.

4. The automatic drug packaging machine and package-less verification system of claim 3 wherein creating the record for the pouch package during formation of the pouch package web occurs before the pouch package exits the module.

5. The automatic drug packaging machine and package-less verification system of claim 3 wherein the module is capable of being secured to an automatic drug packaging machine housing.

6. The automatic drug packaging machine and package-less verification system of claim 1 wherein the method further includes creating a record of the pouch package verification or non-verification.

7. The automatic drug packaging machine and package-less verification system of claim 6 wherein creating the record of the pouch package verification or non-verification further includes creating the record in a file for the pouch package.

8. The automatic drug packaging machine and package-less verification system of claim 1 wherein the method further includes generating an alarm if the codes do not match.

9. The automatic drug packaging machine and package-less verification system of claim 1 wherein the method further includes stopping the automatic drug packaging machine if the codes do not match.

10. The automatic drug packaging machine and package-less verification system of claim 1 wherein the method further includes providing a modification of the pouch package if the codes do not match.

11. The automatic drug packaging machine and package-less verification system of claim 10 wherein the modification provided is an identification mark made on the pouch package.

12. The automatic drug packaging machine and package-less verification system of claim 1 wherein the method further includes providing a classification code on the pouch package, the classification code including a color corresponding to the time of day at which each drug in the pouch package is to be taken by a patient.

13. The automatic drug packaging machine and package-less verification system of claim 1 wherein the method further includes providing a message package in the pouch package web proximate the pouch package, the message package including information relating to the pouch package.

14. The automatic drug packaging machine and package-less verification system of claim 1 wherein the applied information is on the side through which each packaged drug is viewable and the applied information and each packaged drug are viewable simultaneously.

15. The automatic drug packaging machine and package-less verification system of claim 1 wherein the machine-readable code of the pouch package is a barcode.

16. The automatic drug packaging machine and package-less verification system of claim 1 wherein the code reader is integrated with the imager.

17. The automatic drug packaging machine and package-less verification system of claim 1 further comprising a display and the comparison of the displayed images with the stored information occurs on the display.

18. The automatic drug packaging machine and package-less verification system of claim 17 including a first location at which the automatic drug packaging machine is located and the capturing of the image of the pouch package occurs and a second location different from and spaced from the first location at which the display is located and at which the comparison occurs.

19. The automatic drug packaging machine and package-less verification system of claim 17 wherein the applied human-readable information is on a pouch package first side, the side through which each packaged drug is viewable is a pouch package second side, and the imager further includes:
 a first imaging device secured with respect to the support structure adjacent the pouch package web to capture an image of the applied information on the pouch package first side; and
 a second imaging device secured with respect to the support structure adjacent the pouch package web to capture the image of the pouch package second side and each packaged drug viewable through the second side.

20. The automatic drug packaging machine and package-less verification system of claim 19 wherein the method further includes:

capturing an image of the applied information on the pouch package first side with the first imaging device;

capturing an image of the pouch package second side through which each packaged drug is viewable with the second imaging device; and the comparison of the images of the pouch package first side, the pouch package second side and the stored information for the pouch package occurs on the display.

21. The automatic drug packaging machine and packageless verification system of claim 20 wherein the method further includes associating an image of the pouch package first side and an image of the pouch package second side with a file for the pouch package.

22. The automatic drug packaging machine and packageless verification system of claim 21 wherein the method further includes creating a record in the file that the pouch package has been verified as correct by a user.

23. The automatic drug packaging machine and packageless verification system of claim 1 wherein the pouch package further includes a side in addition to the side through which each packaged drug is viewable, the information-application device comprises a printer, and the method further includes printing the applied information on a side.

24. The automatic drug packaging machine and packageless verification system of claim 23 wherein the applied information includes a registration mark detectable by the imager and the method further includes capturing the image of the pouch package side including the applied information responsive to detection of the registration mark.

25. The automatic drug packaging machine and packageless verification system of claim 24 wherein the method further includes:

selecting a size for the pouch package from a plurality of different sizes; and printing the applied information including the registration mark on a pouch package side at a position based on the selected pouch package size so that the applied information is in position for imaging by the imager.

26. The automatic drug packaging machine and packageless verification system of claim 1 wherein the automatic drug packaging machine further comprises:

a cassette;

a first counter associated with the cassette, the counter making a count when each drug is dispensed from the cassette;

a second counter associated with the packaging apparatus which receives each drug dispensed from the cassette, the second counter making a count when each drug is loaded into the pouch package web for forming a pouch package; and, wherein, the method further includes comparing the counts with an expected count for the pouch package to confirm that the expected count was packaged in the pouch package.

* * * * *